(12) United States Patent
Fik et al.

(10) Patent No.: US 11,000,454 B2
(45) Date of Patent: *May 11, 2021

(54) DENTAL COMPOSITION

(71) Applicant: DENTSPLY SIRONA inc., York, PA (US)

(72) Inventors: Christoph Fik, Schonenberg a.d. Thur (CH); Maximilian Maier, Constance (DE); Joachim E. Klee, Radolfzell (DE)

(73) Assignee: DENTSPLY SIRONA INC., York, PA (US)

( * ) Notice: Subject to any disclaimer, the term of this patent is extended or adjusted under 35 U.S.C. 154(b) by 39 days.

This patent is subject to a terminal disclaimer.

(21) Appl. No.: 16/302,701

(22) PCT Filed: May 19, 2017

(86) PCT No.: PCT/EP2017/062152
§ 371 (c)(1),
(2) Date: Nov. 19, 2018

(87) PCT Pub. No.: WO2017/198840
PCT Pub. Date: Nov. 23, 2017

(65) Prior Publication Data
US 2019/0117523 A1   Apr. 25, 2019

(30) Foreign Application Priority Data
May 19, 2016 (EP) .................................... 16170375

(51) Int. Cl.
*A61K 6/88* (2020.01)
*A61K 6/887* (2020.01)
*C09D 4/00* (2006.01)
*A61K 6/30* (2020.01)
*A61K 6/62* (2020.01)

(52) U.S. Cl.
CPC ............... *A61K 6/887* (2020.01); *A61K 6/30* (2020.01); *A61K 6/62* (2020.01); *C09D 4/00* (2013.01)

(58) Field of Classification Search
CPC . A61K 6/30; A61K 6/62; A61K 6/887; C09D 4/00
See application file for complete search history.

(56) References Cited

U.S. PATENT DOCUMENTS 10,512,594 B2 * 12/2019 Klee ...................... A61K 6/20
2018/0289592 A1 * 10/2018 Klee ..................... A61K 6/887

FOREIGN PATENT DOCUMENTS

| WO | 2014040729 A1 | 3/2014 |
| WO | 2015067815 A1 | 5/2015 |
| WO | 2017017156 A1 | 2/2017 |

OTHER PUBLICATIONS

PCT International Search Report, application No. PCT/EP2017/062152.
PCT International Written Opinion, application No. PCT/EP2017/062152.
European Search Report, dated Nov. 3, 2016.

* cited by examiner

*Primary Examiner* — Sanza L. McClendon
(74) *Attorney, Agent, or Firm* — Dentsply Sirona Inc.

(57) ABSTRACT

Disclosed here in is a dental composition having a novel polymerizable compound, a photosensitizer and an iodonium salt. Further disclosed are method of preparing a dental composition.

12 Claims, 5 Drawing Sheets

DENTAL COMPOSITION

FIELD OF THE INVENTION

The present invention relates to a polymerizable dental composition comprising a specific polymerizable compound. Furthermore, the present invention relates to the use of the specific polymerizable compound for the preparation of a dental composition. The polymerizable compound of the present invention is a polyfunctional polymerizable monomer, which is copolymerizable with conventional (meth)acrylates, (meth)acrylamides and allylic ethers, and which provides dental compositions having a low viscosity and excellent biocompatibility.

BACKGROUND OF THE INVENTION

Polymerizable dental compositions containing polymerizable compounds are known. Conventionally, polymerizable dental compositions are provided for a broad range of applications and must, therefore, meet diverse requirements. For example, a polymerizable dental composition may be a dental adhesive composition, a bonding agent, a pit and fissure sealant, a dental desensitizing composition, a pulp capping composition, a dental composite, a dental glass ionomer cement, a dental cement, a dental root canal sealer composition or a dental infiltrant.

Typically, (meth)acrylates are used as polymerizable components in polymerizable dental compositions due to their excellent reactivity in radical polymerizations which may be demonstrated based on the polymerization enthalpy in the range of from $\Delta_R H = -80$ to $-120$ kJ/mol. In order to provide crosslinking capability, polyfunctional (meth)acrylates such as bis-GMA, were used for dental applications as early as 1962.

EP 2 895 138 A1 discloses polymerizable dental compositions comprising N-substituted acrylic acid amide compounds having a linker group in the form of a divalent $C_1$ to $C_{20}$ alkylene group optionally containing a carbon-carbon double bond, however without generally defining the position of the carbon-carbon double bond within said alkylene group. EP 2 895 138 A1 only discloses one example for such polymerizable compound, namely N,N'-diallyl-1,4-bisacrylamido-(2E)-but-2-en (BAABE). Further, the polymerizable compounds of EP 2 895 138 A1 comprise an allyl group bonded to a nitrogen atom of a polymerizable (meth)acrylamide group, which allyl group is taught to provide for an advantageous cyclopolymerisation reaction.

The European patent application having the application numbers EP15 178 515 and EP 15 188 969 represent prior art pursuant to Article 54(3) EPC and disclose polymerizable dental compositions which may comprise polymerizable compounds wherein two N-substituted acrylic acid amide moieties are linked via a linker. Said linker may represent a $C_2$ to $C_{12}$ or $C_{18}$ alkenylene group, wherein the position of the carbon-carbon double bond in said alkenylene linker group is not generally defined. As a specific example for the polymerizable compounds having said alkenylene linker, EP 15 178 515 and EP 15 188 969 disclose N,N'-diallyl-1,4-bisacrylamido-(2E)-but-2-en (BAABE).

SUMMARY OF THE INVENTION

It is the problem of the present invention to provide a polymerizable dental composition comprising a specific polymerizable compound which is copolymerizable with conventional (meth)acrylates, (meth)acrylamides and allylic ethers, and which has a favorable polymerization enthalpy, a low viscosity and excellent biocompatibility.

The present invention provides a polymerizable dental composition comprising
(a) a polymerizable compound of the following formula (I):

X'-L-X"     (I)

wherein
X' represents a group of the following formula (II) or (III):

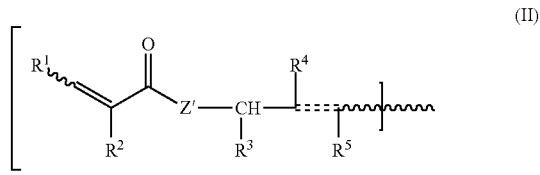

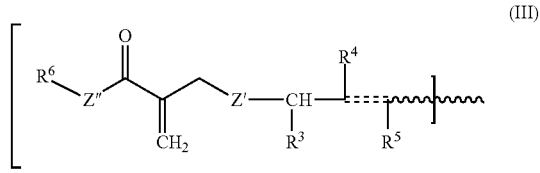

wherein
the dotted lines represent
    a double bond or a triple bond, whereby in case a triple bond
    is present, $R^4$ and $R^5$ are absent;
the jagged line(s) indicate(s) that formula (II) and (III) include any (E) or (Z) isomer,
Z' and Z", which may be the same or different, independently represent an oxygen atom, a sulfur atom or >N—R, wherein
    R is a hydrogen atom, a straight-chain, branched or cyclic alkyl or alkenyl group which group may be substituted by an alkoxy or acidic group, or a group of the following formula (IV):

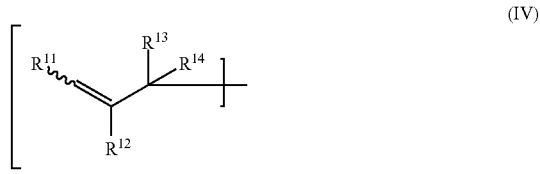

wherein
the jagged line indicates that formula (IV) includes any (E) or (Z) isomer,
$R^{11}$ and $R^{12}$,
    which may be the same or different, independently represent a hydrogen atom or a straight-chain, branched or cyclic alkyl or alkenyl group, which group may be substituted by an alkoxy group or acidic group;
$R^{13}$ and $R^{14}$,
    which may be the same or different, independently represent a hydrogen atom or a straight-chain, branched or cyclic alkyl or alkenyl group, which group may be substituted by an alkoxy or acidic group, or $R^{13}$ and $R^{14}$ represent together an oxygen atom forming a carbonyl group together with the adjacent carbon atom;

$R^1$ and $R^2$,
which may be the same or different, independently represent a hydrogen atom or a straight-chain, branched or cyclic alkyl or alkenyl group, which group may be substituted by at least one moiety selected from the group consisting of a hydroxyl group, an alkoxy group and an acidic group;

$R^3$ represents a hydrogen atom or a straight-chain, branched or cyclic alkyl or alkenyl group, which group may be substituted by an alkoxy or acidic group;

$R^4$ and $R^5$,
which may be the same or different, independently represent a hydrogen atom, a straight-chain, branched or cyclic alkyl or alkenyl group, which group may be substituted by an alkoxy or acidic group;

$R^6$ represents a hydrogen atom or a straight-chain, branched or cyclic alkyl or alkenyl group, which group may be substituted by an alkoxy group;

X" represents a moiety selected from the group consisting of a hydroxyl group, a thiol group, an alkoxy group and an acidic group, or a moiety of the following formula (V) or (VI):

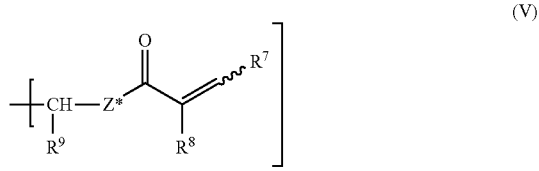

(V)

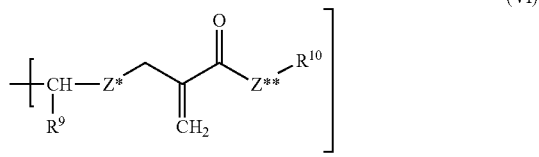

(VI)

wherein
the jagged line indicates that formula (V) includes any (E) or (Z) isomer, $Z^*$ and $Z^{**}$, which may be the same or different, independently represent an oxygen atom, a sulfur atom or >N—R', wherein
R' is a hydrogen atom, a straight-chain, branched or cyclic alkyl or alkenyl group which group may be substituted by an alkoxy or acidic group, or R' independently is a group of the formula (IV) as defined for R;

$R^7$ and $R^8$
which may be the same or different, independently represent a hydrogen atom, a straight-chain, branched or cyclic alkyl or alkenyl group, which group may be substituted by at least one moiety selected from the group consisting of a hydroxyl group, a thiol group, an alkoxy group and an acidic group;

$R^9$ represents a hydrogen atom or a straight-chain, branched or cyclic alkyl or alkenyl group, which group may be substituted by an alkoxy or acidic group;

$R^{10}$ represents a hydrogen atom or a straight-chain, branched or cyclic alkyl or alkenyl group, which group may be substituted by an alkoxy group;

or alternatively,
any two residues of $R^1$, $R^2$, $R^3$, $R^4$, $R^5$, $R^6$, R, $R^7$, $R^8$, $R^9$, $R^{10}$, R', and if present, $R^{11}$, $R^{12}$, $R^{13}$ and $R^{14}$ may represent together an alkylene or alkenylene group, which may be substituted by an alkoxy group, an acidic group or a —NR$^{\blacktriangle}$R$^{\blacktriangledown}$ group wherein R$^{\blacktriangle}$ and R$^{\blacktriangledown}$ Independently from each other represent a hydrogen atom or an alkyl group;
or
any two residues of $R^1$, $R^2$, $R^3$, $R^4$, $R^5$, $R^6$, R, $R^7$, $R^8$, $R^9$, $R^{10}$, R', and if present, $R^{11}$, $R^{12}$, $R^{13}$ and $R^{14}$, which are not geminal or vicinal groups, may represent together a single bond,
wherein said single bond or said optionally substituted alkylene or alkenylene group form together with the bridging atoms to which the residues are linked a 3- to 8-membered saturated or unsaturated ring,
wherein the polymerizable compound of formula (I) may comprise one or more of said 3- to 8-membered saturated or unsaturated ring(s); and L which may be present or absent, represents, when present, a divalent linker group, and when absent X' and X" are bonded directly by a single bond;

(b) a photosensitizer, and
(c) an iodonium salt.

The present invention also provides a use of a polymerizable compound of formula (I) for the preparation of a dental composition.

The present invention is based on the recognition that a polymerizable compound of formula (I) has a polymerization enthalpy which is comparable to or better than the polymerization enthalpy of conventional (meth)acrylates, (meth)acylamides and allylic ethers. Moreover, the present invention is based on the recognition that the viscosity of the compounds of formula (I) is within the range of (meth)acrylates typically applied in the field of dental compositions. In addition, the polymerizable compound of formula (I) provides an advantageous maximum rate of polymerization and desirable mechanical characteristics such as flexural strength.

BRIEF DESCRIPTION OF THE FIGURES

In FIG. 1, RI is depicted by dark grey bars, and the viscosity η by light grey hatched bars. For comparative compound (C1), no viscosity η was determined (indicated by "*"), since this compound is a solid.

In FIG. 4, the E-modulus is depicted by dark grey bars, and flexural strength (FS) by light grey hatched bars. For compound of formula (C3) and (C1), no E-modulus and flexural strength were determined due to pre-test failure (indicated by "*").

DETAILED DESCRIPTION OF PREFERRED EMBODIMENTS

Figure 1:
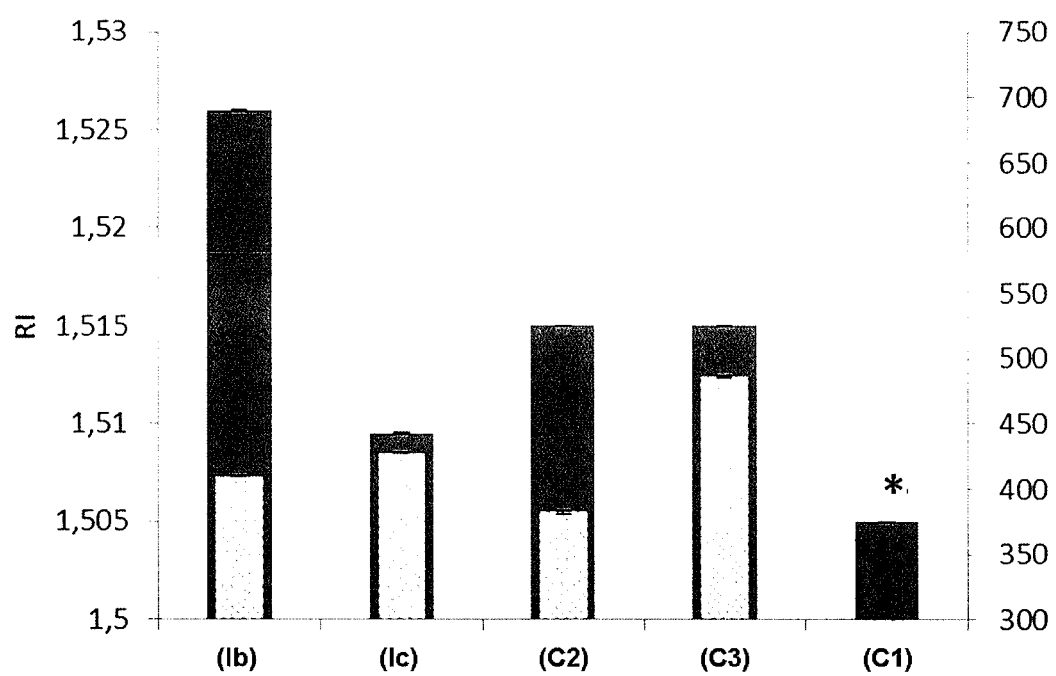
FIG. 1 shows a bar diagram for the parameters refractive index (RI) measured at 20° C. ($n_D^{20}$) and viscosity n measured at 23° C. ($\eta_{23°\,C.}$) for compounds of formula (I) according to the invention denoted as (Ib) and (Ic), and comparative compounds (C1), (C2) and (C3). Compound (Ib) is N,N'-bisacryloyl-N,N'-bisallyl-2,4-pent-2-endiamine, and compound (Ic) is N,N'-bisacryloyl-N,N'-bispropyl-1,4-but-2-endiamine. Comparative compound (C1) is N,N'-bisacetyl-N,N'-bisallyl-1,4-but-2-endiamine, (C2) is N,N'-bisacryloyl-N,N'-bisallyl-1,4-butandiamine, and C(3) is N,N'-bisacryloyl-N,N'-bispropyl-1,4-butandiamine.

The terms "polymerization" and "polymerizable" relate to the combining by covalent bonding of a large number of smaller molecules, such as monomers, to form larger molecules, that is, macromolecules or polymers. The monomers may be combined to form only linear macromolecules or they may be combined to form three-dimensional macromolecules, commonly referred to as crosslinked polymers. For example, monofunctional monomers form linear polymers, whereas monomers having at least two functional groups form crosslinked polymers also known as networks. In case of a higher conversion rate of the polymerizable monomer, the amount of multifunctional monomers may be reduced or the leaching problem may be alleviated.

The term "(E) or (Z) isomer" as used herein means that in formulae (II), (III), (IV) and (V), the substituents which bond is illustrated in the form of a jagged line, may be in (E) or (Z) configuration. The (E) or (Z) configuration is determined as follows. First, priorities are assigned to all substituents bonded to the carbon-carbon double bonds according to the Cahn-Ingold-Prelog priority rules which have a well defined meaning in the art of organic chemistry. Second, the configuration of the substituent which bond is illustrated in the form of a jagged line is determined relative to a substituent located at the adjacent carbon atom of the carbon-carbon double bond. For example, the substituent which bond is illustrated in the form of a jagged line may be in (E) position, that is on a side of the double bond which is opposite (trans-configuration) to a substituent located at the adjacent carbon of the carbon-carbon double bond and having the highest priority there. Alternatively, the substituted which bond is illustrated in the form of a jagged line may be in (Z) position, that is on the same side of the double bond (cis-configuration) as a substituent located at the adjacent carbon of the carbon-carbon double bond and having the highest priority there.

The terms "curing" and "photocuring" mean the polymerization of functional oligomers and monomers, or even polymers, into a crosslinked polymer network. Curing is the polymerization of unsaturated monomers or oligomers in the presence of crosslinking agents.

"Actinic radiation" is any electromagnetic radiation that is capable of producing photochemical action and can have a wavelength of at least 150 nm and up to and including 1250 nm, and typically at least 300 nm and up to and including 750 nm.

The term "photosensitizer" is any chemical compound that forms free radicals when activated, e. g. by exposure to light or interaction with a coinitiator in a photochemical process.

The term "coinitiator" refers to a molecule that produces a chemical change in another molecule such as a photosensitizer in a photochemical process. The coinitiator may be a photosensitizer or an electron donor.

The term "electron donor" as used herein means a compound which is capable of donating electrons in a photochemical process. Suitable examples include organic compounds having heteroatoms with electron lone pairs, for example amine compounds.

The present invention provides a polymerizable dental composition being polymerizable or copolymerizable by a radical polymerization. The polymerizable dental composition may be a dental material to be used in the oral cavity. Preferably, the present polymerizable dental composition is selected from a dental adhesive, a dental primer, a dental resin modified glass ionomer cement, a pit and fissure sealer, a dental composite, or a dental flowable. The dental composition may be cured by irradiation of actinic radiation.

The Polymerizable Compound of Formula (I)

The present polymerizable dental composition comprises a polymerizable compound of formula (I). The polymerizable dental composition may comprise one or more polymerizable compounds of formula (I).

The polymerizable dental composition of the present invention comprises the polymerizable compound(s) of formula (I) in an amount of from 1 to 70 percent by weight based on the total weight of the polymerizable dental composition. Preferably, the polymerizable dental composition comprises one or more compounds of formula (I) in an amount of from 10 to 60 percent by weight, most preferably 20 to 60 percent by weight based on the total weight of the entire polymerizable dental composition.

The amount of compound of formula (I) may be suitably selected in view of the intended application purpose. For example, a dental adhesive may comprise 1 to 70 percent by weight, preferably 20 to 60 percent by weight, based on the total weight of the entire polymerizable dental composition. A dental primer may comprise 1 to 70 percent by weight, preferably 5 to 25 percent by weight, based on the total weight of the entire polymerizable dental composition. A pit and fissure sealant may comprise 1 to 70 percent by weight, preferably 5 to 20 percent by weight, based on the total weight of the entire polymerizable dental composition. A dental glass ionomer cement may comprise 1 to 30 percent by weight, preferably 2 to 10 percent by weight, based on the total weight of the entire polymerizable dental composition.

The (a) polymerizable compound has the following formula (I):

X'-L-X"                    (I).

In formula (I), X' is a specific polymerizable group which is linked by a divalent linker group L to a group X". The group X" may be polymerizable.

According to the present invention, X' is a group of the following formula (II) or (III):

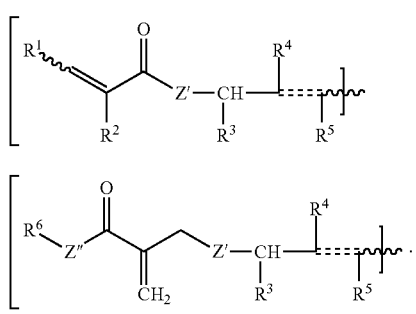

In formula (II) an (III), the dotted lines represent a double bond or a triple bond, preferably a double bond. In case a triple bond is present, $R^4$ and $R^5$ are absent.

The jagged line(s) indicate(s) that formula (II) and (III) include any (E) or (Z) isomer. In case the dotted lines in formula (III) represent a triple bond, then there is no (E) or (Z) isomerism at the moiety $CR^4\!=\!CR^5$.

Specifically, in formula (II) and (III), $R^1$ may be in (E) or (Z) configuration, for example relative to the carbonyl group. Further, if the bond between $CR^4$ and $CR^5$ is a double bond, then the jagged line/line may be in (E) or (Z) configuration, for example relative to the moiety —$CHR^3$—. Preferably, $R^1$ is in (E) configuration relative to the substituent at the adjacent carbon atom of the carbon-carbon double bond having the highest priority according to the Cahn-Ingold-Prelog priority rules, which is either $R^2$ or the carbonyl group. Further, if the bond between $CR^4$ and $CR^5$ is a double bond, then it is preferred that the substituent bonded to the carbon-carbon double bond by the jagged line/bond has a higher priority than substituent $R^5$, and the jagged line/bond is in (E) configuration relative to the substituent at the adjacent carbon atom of the carbon-carbon double bond having the highest priority according to the Cahn-Ingold-Prelog priority rules, which is either $R^4$ or the moiety —$CHR^3$—.

Accordingly, any compound of formula (I) is characterized by a (meth)acryl group of formula (II) and/or (V) or inverse (meth)acryl group of formula (III) and/or (VI), and a double or triple bond imparting C—H acidity to the hydrogen atom of the adjacent moiety —$CHR^3$—. Without wishing to be bound to theory, it is believed that this C—H acidity, in combination with the polymerizable C—C double bond of the (Inverse) (meth)acryl group provides for the particularly advantageous polymerization enthalpy and viscosity of compound of formula (I). In addition, owing to the above described C—H acidity, the compound of formula (I) provides an advantageous maximum rate of polymerization and desirable mechanical characteristic such as flexural strength.

C—H acidity may be impaired by internal and external N-allyl groups. It was surprisingly found that the C—H acidity of the hydrogen atom of the moiety —$CHR^3$— is less prone to impairment by internal and external N-allyl groups e.g. when the double or triple bond represented together by $CR^4$ and $CR^5$ is located between Z'=N—R and Z*=N—R'. Therefore, in order to provide an advantageous CH-acidity, in present formula (I), the aforementioned double or triple bond is located between Z and Z* which may form an N-allyl group when representing N—R and Z* =N—R'.

In prior art EP 2 895 138 A1, there is no general teaching for the position of the C—C double bond in the linker of the polymerizable compound, since the above explained effect of the C—H acidity was not recognized. Instead, EP 2 895 138 A1 teaches that an allyl group has to be mandatory bonded to the nitrogen of a polymerizable (meth)acrylamide unit for rendering possible an advantageous cyclopolymerization reaction.

$R^1$ and $R^2$ of formula (II) and (III) may be the same or different, and independently represent a hydrogen atom or a straight-chain, branched or cyclic alkyl or alkenyl group, which group may be substituted by at least one moiety selected from the group consisting of a hydroxyl group, an alkoxy group and an acidic group.

$R^3$ of formula (II) and (III) represents a hydrogen atom or a straight-chain, branched or cyclic alkyl or alkenyl group, which group may be substituted by an alkoxy or acidic group.

$R^4$ and $R^5$ of formula (II) and (III) may be the same or different, and independently represent a hydrogen atom, a straight-chain, branched or cyclic alkyl or alkenyl group, which group may be substituted by an alkoxy or acidic group.

$R^6$ of formula (II) and (III) represents a hydrogen atom or a straight-chain, branched or cyclic alkyl or alkenyl group, which group may be substituted by an alkoxy group.

Z' and Z", which may be the same or different, independently represent an oxygen atom, a sulfur atom or >N—R, wherein R is a hydrogen atom, a straight-chain, branched or cyclic alkyl or alkenyl group which group may be substituted by an alkoxy or acidic group. Alternatively, R is a group of the following formula (IV):

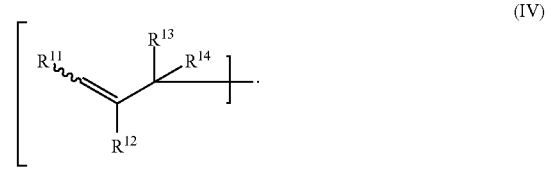

Preferably, Z' and/or Z" represent >N—R wherein R represents a group of formula (IV), most preferably a group of formula (IV) wherein $R^{11}$, $R^{12}$, $R^{13}$ and $R^{14}$ represent hydrogen atoms, that is group (IV) is an unsubstituted allyl group. Because, said group of formula (IV) or allyl group may take part together with the polymerizable carbon-carbon double bond of the (meth)acryl group of formula (II) or the inverse (meth)acryl group of formula (III) in a cyclopolymerization reaction according to the following Scheme 1:

Scheme 1: Intramolecular cyclopolymerization of compound of formula (I) wherein X' = group of formula (II) in which
Z' = >N—R with R = group of formula (IV) wherein
$R^{11} = R^{12} = R^{13} = R^{14}$ = hydrogen atom.

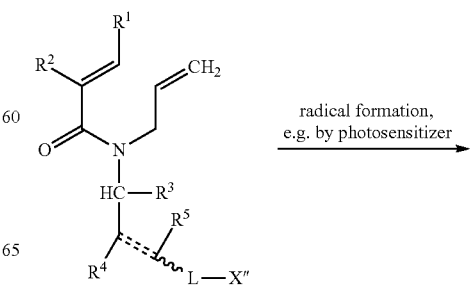

radical formation,
e.g. by photosensitizer

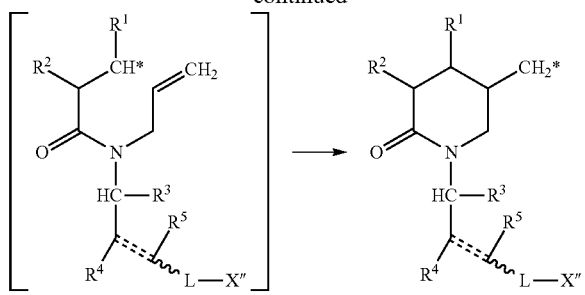

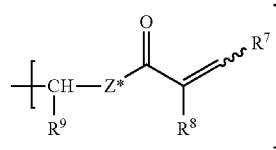

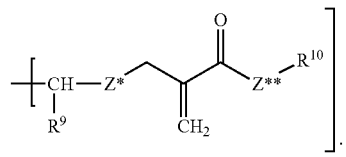

The formation of rings by means of the above cyclopolymerization can be verified for example by means of infrared spectroscopy (IR) alone or in combination with a further analytical method, for example nuclear magnetic resonance spectroscopy (NMR).

The intramolecular cyclopolymerization of N-allylacrylamides is known in the field of chemistry and described e.g. by L. Trossarelli at al., "Free Radical Polymerization of unconjugated Dienes: III. N-Allylacrylamide in Methanol", Die Makromolekulare Chemie, 1967, vol. 100, pages 147 to 155, or by W. Fukuda, "Cyclopolymerization of N-Alkyl-N-allylacrylamides", Polymer Journal, 1988, vol. 20, no. 4, pages 337 to 344.

Without wishing to be bound to theory, the above described cyclopolymerzation may result in the formation of a reduced number of polymeric network points, that is a reduced crosslinking density, compared to compounds of formula (I) having no group R in the form of an alkylene group such as the group of formula (IV). This in turn may provide for a reduced polymerisation stress as compared with comparable compounds of formula (I) having identical molar mass and identical amount(s) of polymerizable double bond(s), but no group Z' and/or Z" being >N—R wherein R represents a group of formula (IV), specifically an allyl group.

The jagged line indicates that formula (IV) includes any (E) or (Z) isomer. Specifically, $R^{11}$ may be in (Z) or (E) configuration, for example relative to the moiety $CR^{13}R^{14}$. Preferably, $R^{11}$ is in (E) configuration relative to the substituent at the adjacent carbon atom of the carbon-carbon double bond having the highest priority according to the Cahn-Ingold-Prelog priority rules, which may either be $R^{12}$ or the moiety $CR^{13}R^{14}$.

$R^{11}$ and $R^{12}$ of formula (IV) may be the same or different and independently represent a hydrogen atom or a straight-chain, branched or cyclic alkyl or alkenyl group, which group may be substituted by an alkoxy group or acidic group.

$R^{13}$ and $R^{14}$ of formula (IV), which may be the same or different, independently represent a hydrogen atom or a straight-chain, branched or cyclic alkyl or alkenyl group, which group may be substituted by an alkoxy or acidic group. Alternatively, $R^{13}$ and $R^{14}$ of formula (IV) represent together an oxygen atom forming a carbonyl group together with the adjacent carbon atom.

In formula (I), X" represent a moiety selected from the group consisting of a hydroxyl group, a thiol group, an alkoxy group and an acidic group, or a moiety of the following formula (V) or (VI):

The jagged line indicates that formula (V) includes any (E) or (Z) isomer. Specifically, in formula (V), $R^7$ may be in (Z) or (E) configuration relative to the substituent at the adjacent carbon atom of the carbon-carbon double bond having the highest priority according to the Cahn-Ingold-Prelog priority rules, which may either be $R^8$ or the carbonyl group.

$R^7$ and $R^8$ of formula (V) and (VI) may be the same or different, and independently represent a hydrogen atom, a straight-chain, branched or cyclic alkyl or alkenyl group, which group may be substituted by at least one moiety selected from the group consisting of a hydroxyl group, a thiol group, an alkoxy group and an acidic group.

$R^9$ of formula (V) and (VI) represents a hydrogen atom or a straight-chain, branched or cyclic alkyl or alkenyl group, which group may be substituted by an alkoxy or acidic group.

$R^{10}$ of formula (V) and (VI) represents a hydrogen atom or a straight-chain, branched or cyclic alkyl or alkenyl group, which group may be substituted by an alkoxy group.

Z* and Z** of formula (V) and (VI), which may be the same or different, independently represent an oxygen atom, a sulfur atom or >N—R', wherein R' is a hydrogen atom, a straight-chain, branched or cyclic alkyl or alkenyl group which group may be substituted by an alkoxy or acidic group. Alternatively, R' is a group of the formula (IV) as defined for R of Z' and Z" of formula (II) and (III), and is independently selected from R of Z' and Z" of formula (II) and (III). Preferably, formula (IV) of R' of formula (V) and (VI) is identical with formula (IV) of R of formula (II) and (III).

Preferably, Z* and/or Z** represent >N—R' wherein R' represents a group of formula (IV), most preferably a group of formula (IV) wherein $R^{11}$, $R^{12}$, $R^{13}$ and $R^{14}$ represent hydrogen atoms, that is group (IV) is an unsubstituted allyl group. Because, said group of formula (IV) or allyl group may take part together with the polymerizable carbon-carbon double bond of the methacryl group of formula (IV) or the inverse methacryl group of formula (V) in a cyclopolymerization reaction as described above in connection with Z' and Z".

The groups ">N—R" and ">N—R'" defined for Z' and Z" denote a tertiary amine group wherein a residue R or R' is bonded to the nitrogen atom which is incorporated in formula (II), (III), (V) and (VI) via two bonds/valencies indicated by ">". Alternatively, Instead of ">N—R" and ">N—R'", the denotations "—N(—R)—" and "—N(—R')—" may be used.

The "straight-chain, branched or cyclic alkyl or alkenyl group" for $R^1$, $R^2$, $R^3$, $R^4$, $R^5$, $R^6$, R, $R^{11}$, $R^{12}$, $R^{13}$, $R^{14}$ of formula (II) and (III), and $R^7$, $R^8$, $R^9$, $R^{10}$, $R^{11}$, $R^{12}$, $R^{13}$, $R^{14}$, R' of formula (V) and (VI) is not particularly limited. Preferably, this "straight-chain, branched or cyclic alkyl or alkenyl group" represents a straight chain $C_{1-16}$ as or branched or cyclic $C_{3-8}$ alkyl group or a straight chain $C_{2-16}$ or branched or cyclic $C_{3-8}$ alkenyl group, more preferably a straight chain $C_{1-8}$ or branched or cyclic $C_{3-6}$ alkyl group or a straight chain $C_{2-8}$ or branched or cyclic $C_{3-6}$ alkenyl group, most preferably a straight chain $C_{1-4}$ or branched or cyclic $C_{4-6}$ alkyl group or a straight chain $C_{2-4}$ or branched or cyclic $C_{4-6}$ alkenyl group.

Illustrative examples for straight chain or branched alkyl groups are methyl, ethyl, n-propyl, i-propyl, n-butyl, isobutyl, tert-butyl, sec-butyl, pentyl or hexyl, and for the straight chain or branched alkenyl group ethenyl, n-propenyl, i-propenyl, n-butenyl, isobutenyl, tert-butenyl sec-butenyl, pentenyl or hexenyl.

The term "alkenyl" as used herein in connection with $R^1$, $R^2$, $R^3$, $R^4$, $R^5$, $R^6$, R, $R^{11}$, $R^{12}$, $R^{13}$, $R^{14}$ of formula (II) and (III) and $R^7$, $R^8$, $R^9$, $R^{10}$, $R^{11}$, $R^{12}$, $R^{13}$, $R^{14}$, R' of formula (V) and (VI) means a monovalent group derived from a hydrocarbon having the above defined carbon number. This alkenyl group preferably contains at least one carbon-carbon double bond, more preferably 1 to 3 carbon-carbon double bonds, even more preferably 1 or 2 carbon-carbon double bonds, most preferably one carbon-carbon bond. Furthermore, it is preferred that at least one carbon-carbon double bond of the alkenyl group is located between second and third carbon atoms adjacent to a first carbon which attaches the alkenyl group to compound of formula (I).

The most preferred alkenyl groups for $R^1$, $R^2$, $R^3$, $R^4$, $R^5$, $R^6$, R, $R^{11}$, $R^{12}$, $R^{13}$, $R^{14}$ of formula (II) and (III) and $R^7$, $R^8$, $R^9$, $R^{10}$, $R^{11}$, $R^{12}$, $R^{13}$, $R^{14}$, R' of formula (V) and (VI), which may be the same or different, are independently selected from the group consisting of allyl, 1 cyclopropane-1-yl, 2-cyclopropane-1-yl, 1-cyclobutane-1-yl, 2-cyclobutane-1-yl, 1-cyclopentane-1-yl, 2-cyclopentane-1-yl, 3-cyclopentane-1-yl, 1,3-cyclopentadiene-1-yl, 2,4-cyclopentadiene-1-yl, 1-cycloxene-1-yl, 2-cycloxene-1-yl, 3-cycloxene-1-yl, 1,3-cycloheadiene-1-yl and 2,5-cyclohexadiene-1-yl.

The "alkoxy group" defined for $R^1$, $R^2$, $R^3$, $R^4$, $R^5$, $R^6$, R, $R^{11}$, $R^{12}$, $R^{13}$, $R^{14}$ of formula (II) and (III) and $R^7$, $R^8$, $R^9$, $R^{10}$, $R^{11}$, $R^{12}$, $R^{13}$, $R^{14}$, R' of formula (V) and (VI) is not particularly limited. Preferably, said alkoxy group is a straight chain $C_{1-16}$ or branched or cyclic $C_{3-8}$ alkoxy group, more preferably a straight chain $C_{1-8}$ or branched or cyclic $C_{3-6}$ alkoxy group, most preferably a straight chain $C_{1-4}$ or branched or cyclic $C_{4-6}$ alkoxy group. Illustrative examples for $C_{1-6}$ alkoxy groups are methoxy, ethoxy, propoxy, isopropyloxy, cyclopropyloxy, cyclobutyloxy, cyclopentyloxy and cycohexyloxy.

The term "acidic group" as used herein in connection with $R^1$, $R^2$, $R^3$, $R^4$, $R^5$, $R^6$, R, $R^{11}$, $R^{12}$, $R^{13}$, $R^{14}$ of formula (II) and (III) and $R^7$, $R^8$, $R^9$, $R^{10}$, $R^{11}$, $R^{12}$, $R^{13}$, $R^{14}$, R' of formula (V) and (VI) means any group imparting acidity in terms of proton donation capability to the compound of formula (I). Preferably, this acidic group is independently selected from a carboxylic acid group, a sulfonic acid group, a phosphonic acid group and a phosphoric acid monoester group ($—O—P(=O)(OH)_2$).

The following are preferred groups of formula (II) and (III), wherein R and $R^3$ are defined as above:

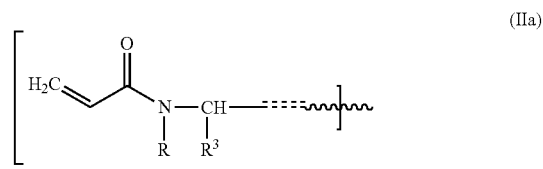
(IIa)

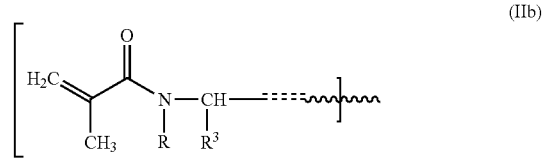
(IIb)

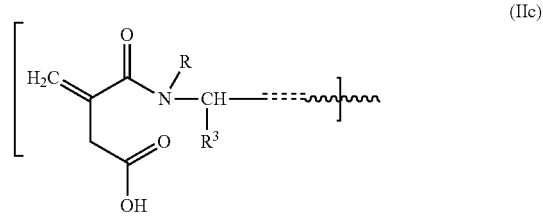
(IIc)

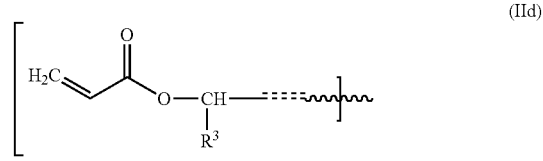
(IId)

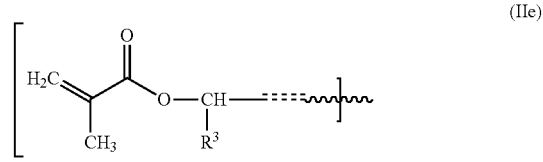
(IIe)

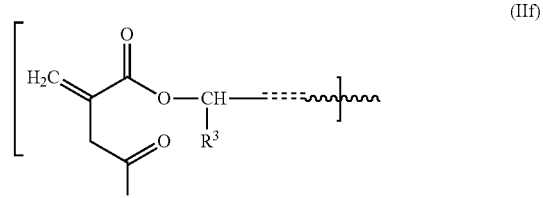
(IIf)

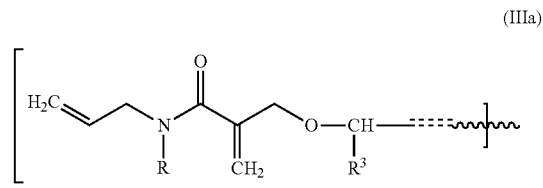
(IIIa)

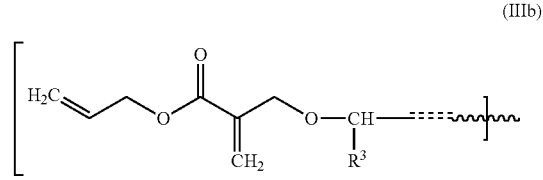
(IIIb)

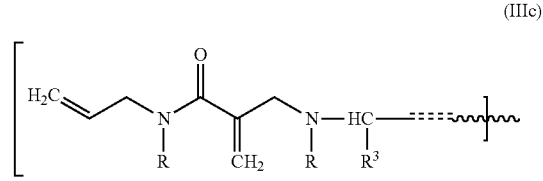
(IIIc)

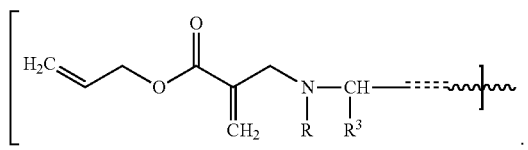
(IIId)

In formula (IIa), (IIb), (IIc), (IId), (IIe), (IIf), (IIIa), (IIIb), (IIIc), (IIId), $R^3$ preferably represents a hydrogen atom, and R preferably represents a hydrogen atom, methyl, ethyl or n-propyl which may optionally be substituted with an acidic group, allyl, 2-cyclopropane-1-yl, 2-cyclobutane-1-yl, 2-cyclopentane-1-yl, 2,4-cyclopentadiene-1-yl, 2-cycloxene-1-yl and 2,5-cyclohexadiene-1-yl.

The groups of formula (IIa) and (IIIa) are particularly preferred.

The following are preferred groups of formula (V) and (VI), wherein R' and $R^9$ are defined as above:

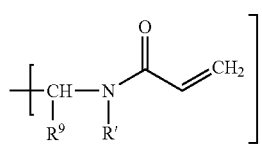
(Va)

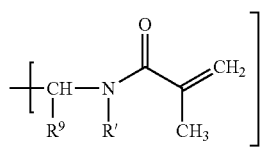
(Vb)

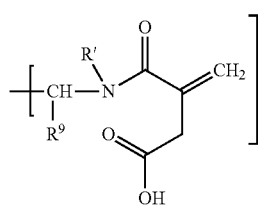
(Vc)

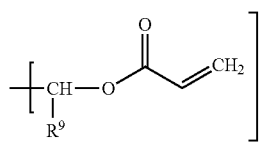
(Vd)

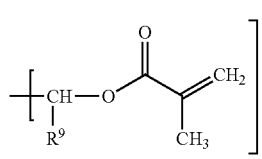
(Ve)

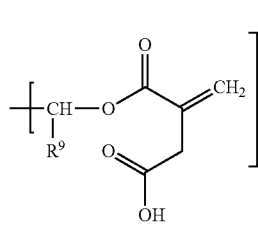
(Vf)

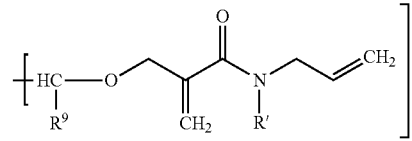
(VIa)

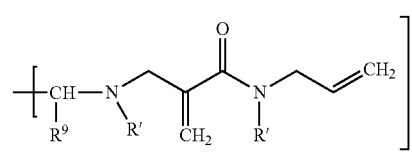
(VIb)

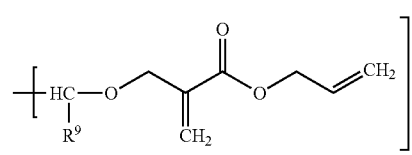
(VIc)

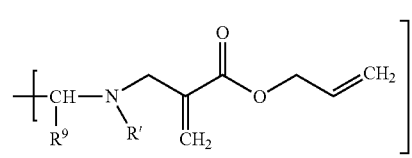
(VId)

In formula (Va), (Vb), (Vc), (Vd), (Ve), (Vf), (VIa), (VIb), (VIc) and (VId), $R^9$ preferably represents a hydrogen atom, and R' preferably represents a hydrogen atom, methyl, ethyl or n-propyl which may optionally be substituted with an acidic group, allyl, 1-cyclopropene-3-yl, 1-cyclobutene-3-yl, 1-cyclopentene-3-yl, 1,3-cyclopentadiene-5-yl, 1-cycloxene-3-yl and 1,4-cyclohexadiene-6-yl.

The groups of formula (Va) and (Via) are particularly preferred.

Preferably, if X' of the compound of formula (I) represents a group of formula (II), then X" represents a group of formula (V), and if X' represents a group of formula (III), then X" represents a group of formula (VI).

It is preferred that $R^{13}$ and $R^{14}$ in R of formula (II) and (III) and/or R' of formula (V) and (VI) represent together an oxygen atom forming a carbonyl group together with the adjacent carbon atom.

In formula (I), alternatively to the above definitions for residues $R^1$, $R^2$, $R^3$, $R^4$, $R^5$, $R^6$, R, $R^7$, $R^8$, $R^9$, $R^{10}$, R', $R^{11}$, $R^{12}$, $R^{13}$ and $R^{14}$, any two of these residues may form a ring together with the bridging atoms to which the residues are linked. Specifically, any two residues of $R^1$, $R^2$, $R^3$, $R^4$, $R^5$, $R^6$, R, $R^7$, $R^8$, $R^9$, $R^{10}$, R', and if present, $R^{11}$, $R^{12}$, $R^{13}$ and $R^{14}$ may represent together an alkylene or alkenylene group which may be substituted by an alkoxy group, and acidic group or a —$NR^{\blacktriangle}R^{\blacktriangledown}$ group wherein $R^{\blacktriangle}$ and $R^{\blacktriangledown}$ independently from each other represent a hydrogen atom or an alkyl group.

Alternatively, any two residues of $R^1$, $R^2$, $R^3$, $R^4$, $R^5$, $R^6$, R, $R^7$, $R^8$, $R^9$, $R^{10}$, R', and if present, $R^{11}$, $R^{12}$, $R^{13}$ and $R^{14}$, which are not geminal or vicinal groups, may represent together a single bond.

The above described single bond or the above described optionally substituted alkylene or alkenylene group may form together with the bridging atoms to which the residues are linked a 3- to 8-membered saturated or unsaturated ring, wherein the polymerizable compound of formula (I) may comprise one or more of said 3- to 8-membered saturated or unsaturated ring(s).

In connection with the above described ring formation of any two of residues $R^1$, $R^2$, $R^3$, $R^4$, $R^5$, $R^6$, R, $R^7$, $R^8$, $R^9$, $R^{10}$, R', $R^{11}$, $R^{12}$, $R^{13}$ and $R^{14}$, the "alkoxy group" with which the alkylene or alkenylene group formed by two of these residues may be substituted is preferably a $C_{1-6}$ alkoxy group, more preferably a $C_{1-3}$ alkoxy group such as methoxy, ethoxy, n- or iso-propoxy, and the "alkyl group" of the "—NR▲R▼ group" is preferably a $C_{1-6}$ alkyl group, more preferably a $C_{1-3}$ alkyl group, such as methyl, ethyl, n- or iso-propyl.

The phrase "if present, $R^{11}$, $R^{12}$, $R^{13}$ and $R^{14}$" as used herein means that if Z' or Z'' represent >N—R with R being formula (IV) and/or for Z* or Z** represent >N—R' with R' being formula (IV), then residues $R^{11}$, $R^{12}$, $R^{13}$ and $R^{14}$ of formula (IV) may form a ring as described above with any one of $R^1$, $R^2$, $R^3$, $R^4$, $R^5$, $R^6$, R, $R^7$, $R^8$, $R^9$, $R^{10}$, R'. However, it is readily understood that R represented by formula (IV) cannot form a ring with itself, i.e. with its residues $R^{11}$, $R^{12}$, $R^{13}$ and $R^{14}$. This likewise applies for R' represented by formula (IV).

The term "geminal groups" as used herein means that two residues are bound to the same atom.

The term "vicinal groups" as used herein means that two residues are respectively bound to adjacent atoms.

Preferably, in formula (II) or (III) of compound of formula (I), any two residues of $R^1$, $R^2$, $R^3$, $R^4$, $R^5$, $R^6$, R may represent together an alkylene or alkenylene group forming together with the bridging atoms to which they are linked a 3- to 8-membered saturated or unsaturated ring, wherein the alkylene or alkenylene group may be substituted by an alkoxy group, an acidic group or a —NR▲R▼ group wherein R▲ and R▼ independently from each other represent a hydrogen atom or an alkyl group.

Likewise, it is preferred for formula (V) or (VI) of compound of formula (I) that any two residues of $R^7$, $R^8$, $R^9$, $R^{10}$, R' may represent together an alkylene or alkenylene group forming together with the bridging atoms to which they are linked a 3- to 8-membered saturated or unsaturated ring wherein the alkylene or alkenylene group may be substituted by an alkoxy, an acidic group or a —NR▲R▼ group wherein R▲ and R▼ independently from each other represent a hydrogen atom or an alkyl group.

Besides of the above preferred ring formations for formula (II) or (III) and (V) or (VI), residues which are not geminal or vicinal groups may represent together a single bond forming together with the bridging atoms to which the residues are linked a 3- to 8-membered saturated or unsaturated ring. Specifically, residues $R^1$, $R^2$ or $R^6$ together with any one of residues $R^3$, $R^4$, $R^5$ and R of Z', residues $R^7$, $R^8$ or $R^{10}$ together with $R^9$ or R' of Z*, or residues $R^3$ and $R^9$, $R^4$ and $R^9$, $R^{11}$ and $R^{13}$ or $R^{14}$ may form together a single bond forming together with the bridging atoms to which they are linked a 3- to 8-membered saturated or unsaturated ring.

More preferably, in formula (I), one or more rings are formed within formula (II)/(111) and/or formula (V)I(VI), wherein it is preferred that one ring is formed in formula (II) or (III) and one ring is formed in formula (V) or (VI). Specifically, any two residues $R^1$, $R^2$, $R^3$, $R^4$, $R^5$, $R^6$, R in formula (II) or (III) and/or any two residues of $R^7$, $R^8$, $R^9$, $R^{10}$, R' in formula (V) or (VI) may represent together an alkylene or alkenylene group forming together with the bridging atoms to which they are linked a 3- to 8-membered saturated or unsaturated ring, wherein the alkylene or alkenylene group may be substituted by an alkoxy group, an acidic group or a —NR▲R▼ group wherein R▲ and R▼ independently from each other represent a hydrogen atom or an alkyl group.

Furthermore, alternatively or in addition to the above described more preferred ring formations within formula (II)/(III) and formula (V)/(VI), rings may be formed between residues of formula (II)/(III) and residues of formula (V)/(VI). Specifically, residue $R^1$, $R^2$ or $R^6$ may represent together with any one of residues $R^3$, $R^4$, $R^5$ and R of Z' a single bond or an optionally substituted alkylene or alkenylene group as described above, wherein said residues form together with the bridging atoms to which they are linked a 3- to 8-membered saturated or unsaturated ring.

In the compound of formula (I), L may be present or absent. When present, L represents a divalent linker group, and when absent X' and X'' are bonded directly by a single bond.

Preferably, L is a group of the following formula (VII)

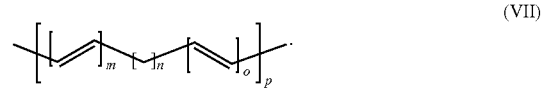

(VII)

In formula (VII), m, n and o, which may be the same or different are integers of from 0 to 3; and p is 0, 1 or 2. Preferably, p is 0 or 1. Further, it is preferred that n is 0. For m and o, it is preferred that m or o is 0. Preferably, in formula (VII) m is 0, n is 0 or 1 and o is 0 to 3, more preferably m is 0, n is 0 or 1 and o is 0 or 1. Most preferably, in formula (VII), m=n=o=0, that is L is absent and X' and X'' are bonded directly by a single bond.

The compound of formula (I) may for example be readily prepared by means of a synthesis route as shown in Scheme 2:

Scheme 2: Exemplary synthesis route for preparing compound of formula (I)

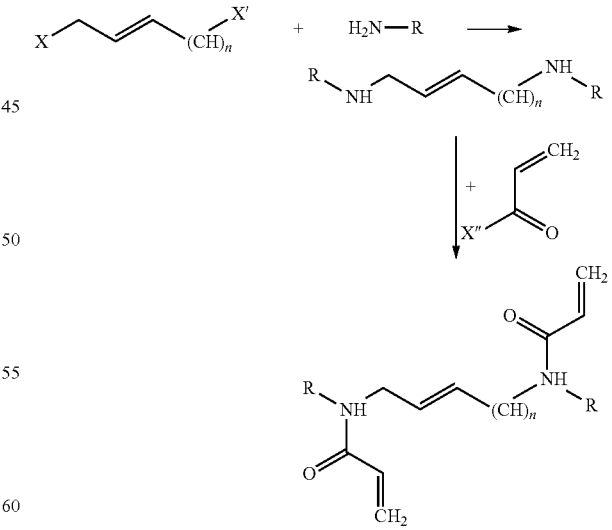

In Scheme 1, the synthesis route is exemplary depicted for the preparation of a compound of formula (I) wherein X' represents a group of formula (II) wherein $R^1$, $R^2$, $R^3$, $R^4$ and $R^5$ are hydrogen atoms, X'' represents a group of formula (V) wherein $R^7$, $R^8$ and $R^9$ are hydrogen atoms, R' and R are identical, and L is a single bond. X and X' represent suitable leaving groups which may for example be halogens such as Cl, Br, I, alkoxy, hydroxyl, alkyl- or aryl-sulfonic acid esters such as mesylate, tosylate and triflate, and X" may be a halogen atom such as Cl, Br and I. It is understood that instead of groups $R^1$, $R^2$, $R^3$, $R^4$, $R^5$, $R^7$, $R^8$ and $R^9$ representing hydrogen atoms, these groups can be varied and may also represent residues other than a hydrogen atom, namely such as defined above for said groups. Furthermore, it is understood that for obtaining compounds of formula (I) wherein $R^1$ is different from $R^7$ and/or $R^3$ is different from $R^8$ and/or R is different from R', one of the leaving groups X and X' may be suitably protected or two leaving groups X and X' having different reactivity may be provided. Then, after subsequent reaction with a first amine compound of formula $H_2N$—R and a first (meth)acrylic acid derivative X"—C(=O)—$CR_2$=$CHR_1$, the protected leaving group X or X' may be deprotected or alternatively, the less reactive, substantially unreacted leaving group X or X' is reacted with a second amine compound of formula $H_2N$—R' and a second (meth)acrylic acid derivative X"—C(=O)—$CR_8$=$CHR_7$. The protecting group of a(n) (optionally) protected leaving group X or X' or protecting groups having different reactivity are not particularly limited and may be any conventional protecting group, for example, described in P. G. M. Wuts and T. W. Greene, Greene's Protective Groups in Organic Synthesis, 4th Edition, John Wiley and Sons Inc., 2007.

It is particularly preferred that in compounds of formula (I), L represents a single bond and the dotted line between $CR^4$ and $CR^5$ represents a double bond, while X' represents a group of formula (II) and X" represents a group of formula (V), or X' represents a group of formula (III) and X" represents a group of formula (VI). Furthermore, it is preferred that in such compound of formula (I), Z represents a group N—R and Z' represents a group N—R'. Most preferably, in compound of formula (I), the selection of $R^1$, $R^2$, $R^3$, $R^4$, $R^5$, $R^6$, $R^{11}$, $R^{12}$, $R^{13}$, $R^{14}$, Z', Z" of formula (II) and (III) is identical with the selection of $R^7$, $R^8$, $R^9$, $R^{10}$, $R^{11}$, $R^{12}$, $R^{13}$, $R^{14}$, Z*, Z** of formula (V) and (VI).

Preferably, residues R and $R^4$ and/or residues R' and $R^5$ may represent together a single bond, an alkylene group or an alkenylene group forming together with the bridging atoms to which they are linked a 3- to 6-membered saturated or unsaturated ring. This ring may be in the form of 1H-azirine-1,3-diyl, 1-azetine-1,3-diyl, 1-pyrolin-1,4-diyl, 1-pyrolin-1,4-diyl, 2-pyrolin-1,4-diyl, 1,2-diyhdropyridine-1,5-diyl, 2,3-diyhdropyridine-1,5-diyl or 3,4-diyhdropyridine-1,5-diyl, more preferably 1-pyrolin-1,4-diyl, 2-pyrolin-1,4-diyl, 1,2-diyhdropyridine-1,5-diyl, 2,3-diyhdropyridine-1,5-diyl or 3,4-diyhdropyridine-1,5-diyl. Preferred rings are in the form of 4- to 6-membered saturated or unsaturated rings in the form of 1-pyrolin-1,4-diyl, 1-pyrolin-1,4-diyl, 2-pyrolin-1,4-diyl, 1,2-diyhdropyridine-1,5-diyl, 2,3-diyhdropyridine-1,5-diyl or 3,4-diyhdropyridine-1,5-diyl, more preferably 1-pyrolin-1,4-diyl, 2-pyrolin-1,4-diyl, 1,2-diyhdropyridine-1,5-diyl, 2,3-diyhdropyridine-1,5-diyl or 3,4-diyhdropyridine-1,5-diyl. Most preferred is 3,4-diyhydropyridine-1,5-diyl. Furthermore, it is preferred that the rings formed by residues R and $R^4$ as well as residues R' and $R^5$ together with the bridging atoms to which they are linked are identical.

Alternatively to the above described ring formation of residues R and $R^4$ and/or residues R' and $R^5$, in formula (I), residues $R^3$ and $R^9$ or residues $R^4$ and $R^9$ may represent together a single bond, an alkylene or alkenylene group forming together with the bridging atoms to which they are linked a 3- to 8-membered saturated or unsaturated ring, wherein it is preferred that 3- to 6-membered unsaturated rings are formed having one or two carbon-carbon-double bonds. Preferably, residues $R^3$ and $R^9$ or residues $R^4$ and $R^9$ form together with L representing a single bond or an alkylene or alkenylene group an unsaturated ring selected from the group consisting of cyclobutene-diyl, cyclopentene-diyl, cyclohexene-diyl and cyclohexadiene-diyl, wherein $R^4$ and $R^9$ may also form a three-membered ring in the form of cyclopropene-diyl.

Alternatively or additionally to the above described ring formations of residues R and $R^4$, residues R' and $R^5$, residues $R^3$ and $R^9$ and residues $R^4$ and $R^9$, if present, any two residues of $R^{11}$, $R^{12}$, $R^{13}$ and $R^{14}$ may form a ring. Preferably, $R^{11}$ may represents together with $R^{13}$ or $R^{14}$ a single bond or an alkylene or alkenylene group forming together with the bridging atoms to which they are linked a 3- to 8-membered saturated or unsaturated ring, wherein it is preferred that 3- to 6-membered unsaturated rings are formed having one or two carbon-carbon-double bonds. Most preferably, $R^{11}$ together with $R^{13}$ or $R^{14}$ form with the bridging atoms to which they are linked a 1-cyclopropene-3-yl, 1-cyclobutene-3-yl, 1-cyclopentene-3-yl, 1,3-cyclopentadiene-5-yl, 1-cycloxene-3-yl and 1,4-cyclohexadiene-6-yl.

For example, compounds of formula (I) may have the following structural formulae, wherein $R^3$, $R^6$, $R^9$, $R^{10}$, R, R', Z', Z", Z*, Z** and o have the same meaning as defined above:

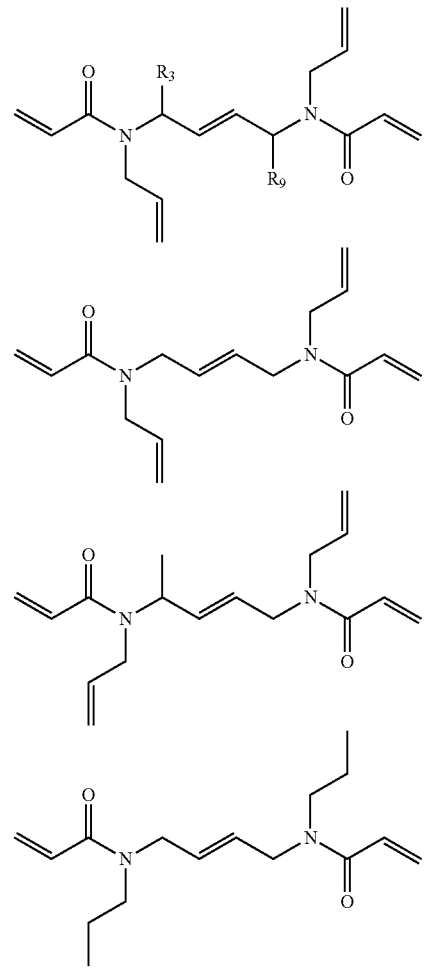

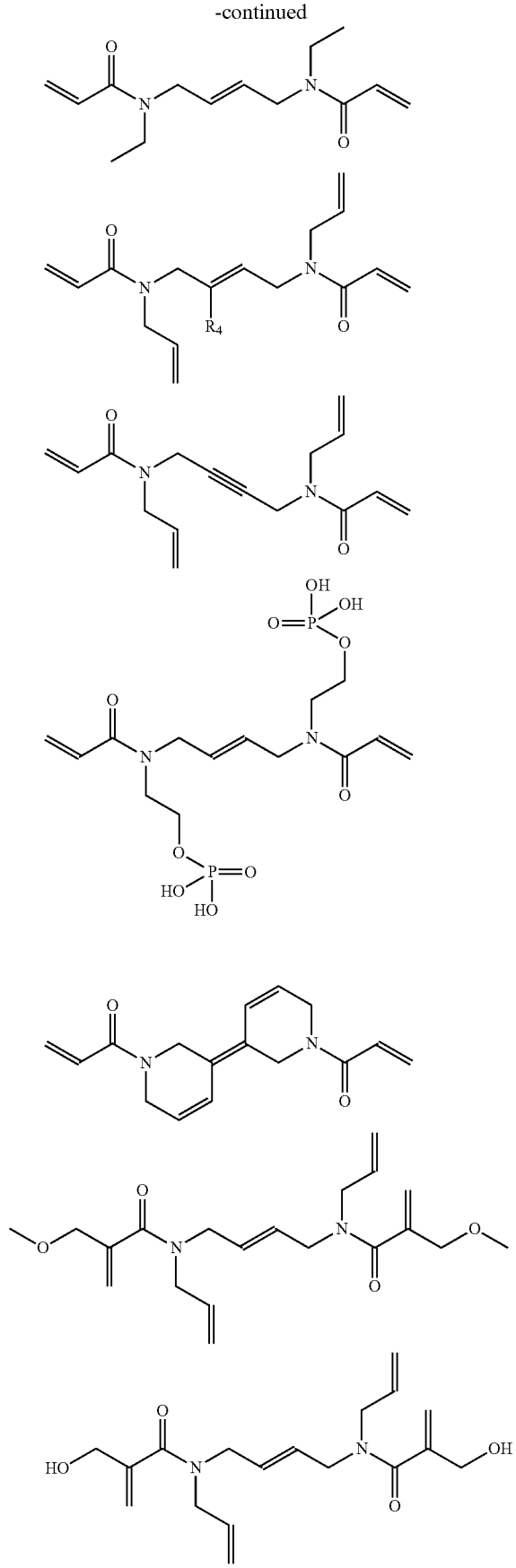
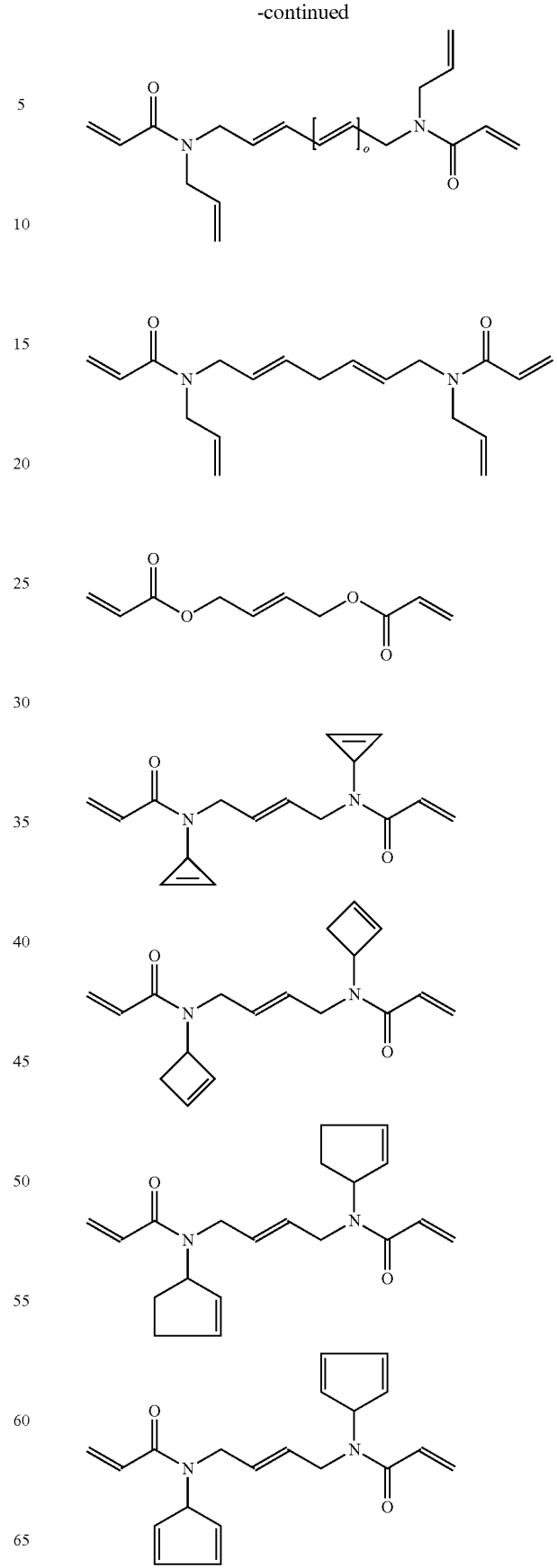

-continued
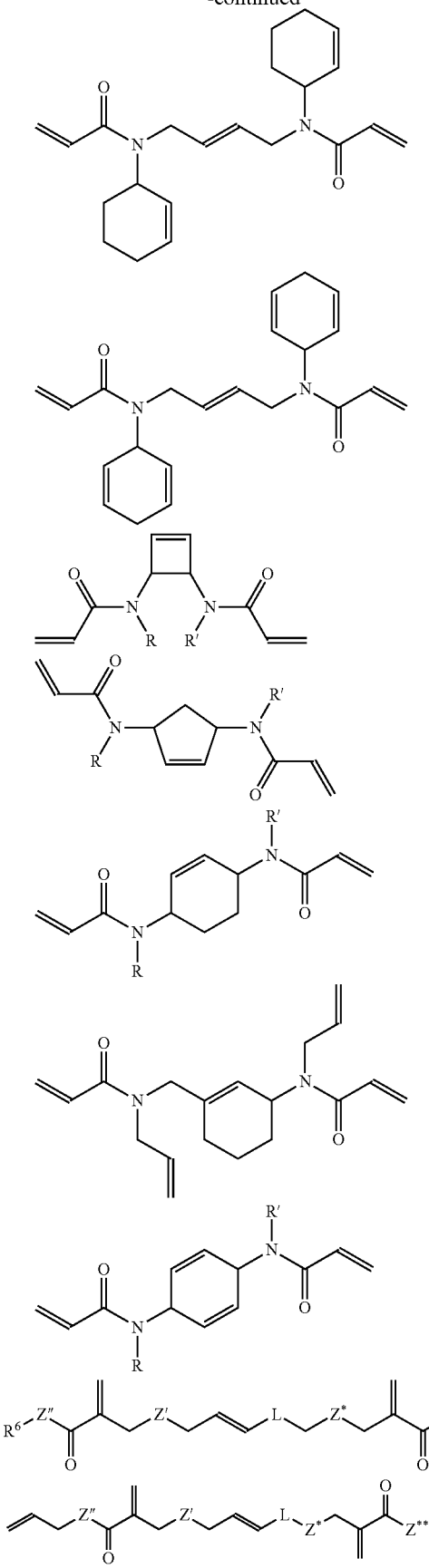
-continued
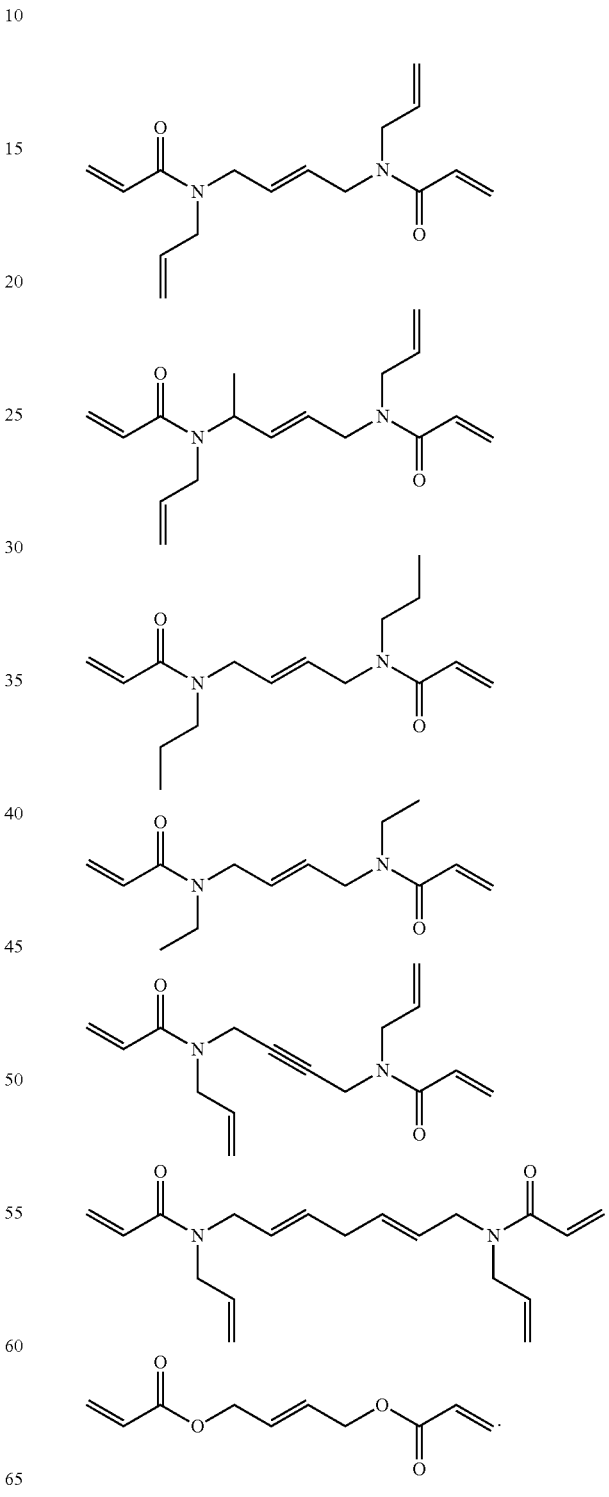
Preferably, compounds of formula (I) have the following structural formulae:

More preferably, compounds of formula (I) have the following structural formulae:

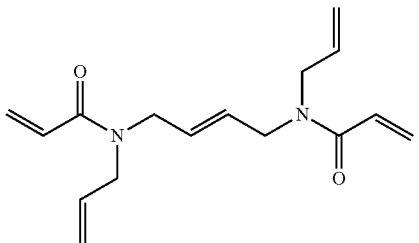

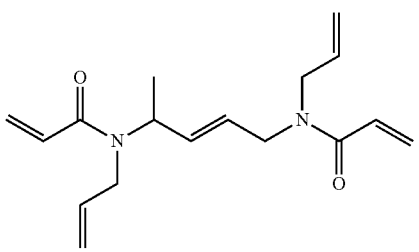

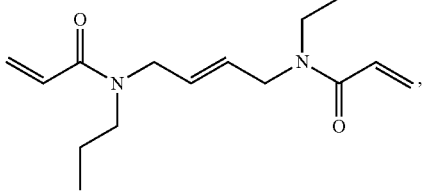

most preferably

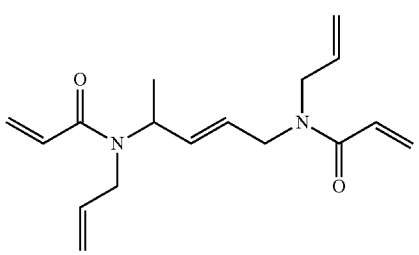

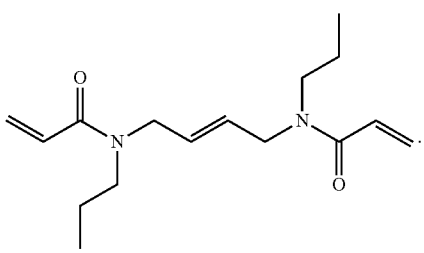

Preferably, the polymerizable compound of the following formula (I) has a refractive index in the range of from 1.500 to 1.580.

It is preferred that the dental composition according to the invention does not contain acrylic acid amide compounds of the following formula (A):

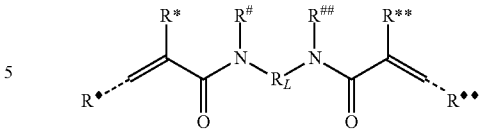

wherein R*, R**, R♦ and R♦♦ which may be the same or different, independently represent a hydrogen atom or a straight-chain, branched or cyclic alkyl group, which group may be substituted by an acidic group, $R^{\#}$ and $R^{\#\#\#}$ which are the same or different, independently represent a hydrogen atom, a straight-chain, branched or cyclic alkyl or alkenyl group which may be substituted by an acidic group, preferably at least one of $R^{\#}$ and $R^{\#\#\#}$ represents an alkenyl group, more preferably an allyl group, and $R_L$ represents a divalent linker in the form of an alkenylene group, preferably a $C_2$ to $C_{20}$ alkenylene group, more preferably a $C_2$ to $C_{20}$ alkenylene group wherein a carbon-carbon double bond is located between a second and a third carbon atom of the alkenylene group which first carbon atom is bonded to any one of the nitrogen atoms of compound of formula (A).

Most preferably, the dental composition according to the invention does not contain a compound of formula (A) in the form of N,N'-diallyl-1,4-bisacrylamido-(2E)-but-2-en (BAABE) and/or N,N'-diallyl-1,4-bismethacrylamido-(2E)-but-2-en, which have the following structural formulae:

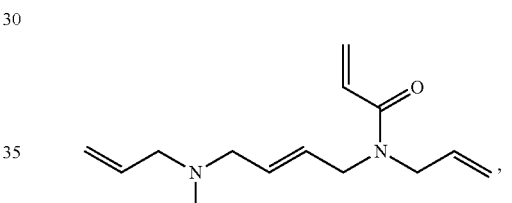

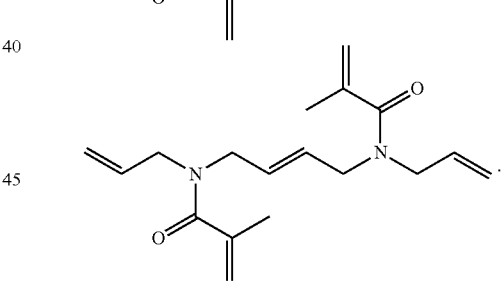

(b) The photosensitizer

The polymerizable dental composition according to the present invention further comprises (b) a photosensitizer. The polymerizable dental composition may comprise (b) one or more photosensitizer(s). The photosensitizer is different from an iodonium salt.

The photosensitizer is not particularly limited. Preferably, the photosensitizer may be selected from a Norrish type I photosensitizer and a Norrish type II photosensitizer.

A Norrish type I photosensitizer is a compound which undergoes excitation by energy absorption with subsequent decomposition of the compound into one or more radicals (Norrish type I). Typical Norrish type I sensitizers are for example phosphine oxides.

A Norrish type II photosensitizer is a compound which undergoes excitation and the excited photosensitizer compound interacts with a second compound by either energy transfer or a redox reaction to form free radicals from any of the compounds. Typical Norrish type II sensitizer are diketones such as 1,2-diketones.

The photosensitizer may be selected from a 1,2-diketone, a phosphine oxide and an acylsilane or acylgermapnium compound.

Suitable phosphine oxide photosensitizers are preferably selected from the group consisting of 2,4-6-trimethylbenzoyl-diphenylphosphine oxide (Irgacure® TPO), 2,4-6-trimethylbenzoyl-diphenylphosphinate (Irgacure® TPO-L, TPO-L), bis(2,4-6-trimethylbenzoyl)-phenylphosphineoxide (Irgacure® BAPO-X). Preferably, the phosphine oxide photosensitizer is 2,4-6-trimethylbenzoyl-diphenylphosphine oxide (Irgacure® TPO).

Suitable examples of 1,2-diketones are preferably selected from the group consisting of camphorquinone, benzil, 2,2'-3,3'- and 4,4'-dihydroxybenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthoquinone, and acenaphthaquinone. Examples of suitable 1,3-diketones are dibenzoyl methane, benzoyl acetone and acetyl propionyl methane. Preferably, the diketone photosensitizer is camphor quinone.

Furthermore, the photosensitizer may by an acylsilane or acylgermanium compound having the following formula (VIII):

wherein
$X^\#$ is a group of the following formula (IX):

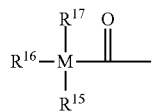

wherein
M is Si or Ge;
$R^{15}$ represents a substituted or unsubstituted hydrocarbyl or hydrocarbylcarbonyl group;
$R^{16}$ represents a substituted or unsubstituted hydrocarbyl or hydrocarbylcarbonyl group;
$R^{17}$ represents a substituted or unsubstituted hydrocarbyl group; and
$R^\#$ (i) has the same meaning as $X^\#$, whereby the compound of formula (VIII) may be symmetrical or unsymmetrical;
or
(ii) is a group of the following formula (X):

wherein
$R^{18}$ represents a substituted or unsubstituted hydrocarbyl group, a trihydrocarbysilyl group, a mono(hydrocarbylcarbonyl)dihydrocarbylsilyl group or a di(hydrocarbylcarbonyl)monohydrocarbylsilyl group, and Y represents a single bond, an oxygen atom or a group $NR^{19}$, wherein $R^{19}$ represents a substituted or unsubstituted hydrocarbyl group;
or
(iii) when M is Si, $R^\#$ may be a substituted or unsubstituted hydrocarbyl group.

It was surprisingly found that compounds of formula (VIII) represent polymerization initiators which are particularly suitable for dental compositions. With compounds of formula (VIII), a high polymerization efficiency is attained, and no coloration problems occur, or in a polymerization system comprising a conventional photosensitizer such as camphor quinone, coloration is efficiently suppressed. Furthermore, compounds of formula (VIII) have a light absorption within the wavelength range typically applied in dental application, they are compatible with the ingredients of dental compositions and besides, they are considered physiologically harmless.

In connection with compound of formula (VIII), the term "substituted" as used herein means that $R^{15}$, $R^{16}$, $R^{17}$, $R^{18}$ and $R^{19}$ may be substituted by a substituent selected from the group consisting of halogen atoms, a nitro group, a cyano group, a hydroxy group, an amino group, $C_{1-6}$ alkyl groups, $C_{1-6}$ alkoxy groups and a —$NR^xR^y$ group wherein $R^x$ and $R^y$ independently from each other represent a $C_{1-6}$ alkyl group. Here, Illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —$NR^xR^y$ group wherein $R^x$ and $R^y$ independently from each other represent a $C_{1-4}$ alkyl group.

If $R^{15}$, $R^{16}$ and $R^{17}$ are substituted, then it is preferred that they are substituted with 1 to 3 substituents, more preferably with 1 substituent.

In the compound of formula (VIII), moieties $R^{15}$, $R^{16}$ and $R^{17}$ may be defined as follows:

$R^{15}$ and $R^{16}$ independently from each other represent a substituted or unsubstituted hydrocarbyl or hydrocarbylcarbonyl group, and $R^{18}$ represents a substituted or unsubstituted hydrocarbyl group.

$R^{19}$ has the same meaning as defined for $R^{17}$ and is independently selected therefrom.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(-) group can for example, include methylcyclopropyl(-) methylcyclobutyl(-), methylcyclopentyl(-), methylcyclohexyl(-), ethylcyclopropyl(-), ethylcyclobutyl(-), ethylcyclopentyl(-), ethylcyclohexyl(-), propylcyclopropyl (-), propylcyclobutyl(-), propylcyclopentyl(-), propylcyclohexyl(-).

An arylalkyl(-) group may be a $C_{7-20}$ arylalkyl(-) group, typically a combination of a linear or branched alkyl group having 1 to 6 carbon atoms and an aryl(-) group having 6 to 10 carbon atoms. Specific examples of an arylalkyl(-) group are a benzyl(-) group or a phenylethyl(-) group.

An aryl group can include aryl groups having 6 to 10 carbon atoms. Examples of the aryl group are phenyl and naphtyl.

The hydrocarbylcarbonyl groups of $R^{15}$ and $R^{16}$ represent acyl groups ($R_{org}$—(C═O)—) in which the organic residue $R_{org}$ is a hydrocarbyl residue as defined above.

Compound of formula (VIII) may contain one or two hydrocarbylcarbonyl groups, that is either one of $R^{15}$ or $R^{16}$ is a hydrocarbylcarbonyl group, or both $R^{15}$ and $R^{16}$ are hydrocarbylcarbonyl groups. Preferably, compound of formula (VIII) contains one hydrocarbylcarbonyl group.

Preferably, the hydrocarbylcarbonyl group is an arylcarbonyl group, more preferably a benzoyl group.

Preferably, $R^{15}$ and $R^{16}$ are independently selected from the group consisting of a straight chain or branched $C_{1-6}$ alkyl group, and a phenyl or benzoyl group which may optionally be substituted by one to three substituents selected from halogen atoms, a nitro group, a $C_{1-4}$ alkoxy group and a —$NR^xR^y$ group wherein $R^x$ and $R^y$ independently from each other represent a $C_{1-4}$ alkyl group, and $R^{17}$ is a straight chain or branched $C_{1-6}$ alkyl group or a phenyl group.

Most preferably, $R^{15}$ and $R^{16}$ are independently selected from the group consisting of a straight chain or branched $C_{1-4}$ alkyl group, and a phenyl or benzoyl group which may optionally be substituted with one substituent selected from the group consisting of selected from a halogen atom, a nitro group, a $C_{1-4}$ alkoxy group and a —$NR^xR^y$ group wherein $R^x$ and $R^y$ independently from each other represent a $C_{1-4}$ alkyl group, and $R^{17}$ is a straight chain or branched $C_{1-4}$ alkyl group.

In the compound of formula (VIII), $R^\#$ may have the same meaning as $X^\#$, whereby the compound of formula (VIII) may be symmetrical or unsymmetrical. Alternatively, $R^\#$ may represent a substituted or unsubstituted hydrocarbyl group, or a group of formula (X). Preferably, if $R^\#$ has the same meaning as $X^\#$, then compound of formula (VIII) is unsymmetrical. If $R^\#$ represents a substituted or unsubstituted hydrocarbyl group, then the hydrocarbyl group has the same meaning as defined above for $R^{15}$ and is independently selected therefrom.

In the group of formula (X) of compound of formula (VIII), $R^{18}$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group.

If $R^{18}$ of formula (X) is a trihydrocarbylsilyl group, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^{15}$, $R^{16}$ and $R^{17}$ and is independently selected therefrom.

If M is Si in compound of formula (VIII), $R^\#$ may be also be a substituted or unsubstituted hydrocarbyl group, wherein the hydrocarbyl group has the same meaning as defined above for $R^{17}$ and is independently selected therefrom.

For example, compounds of formula (VIII) wherein $R^\#$ has the same meaning as $X^\#$ and which are symmetrical may have the following structural formulae:

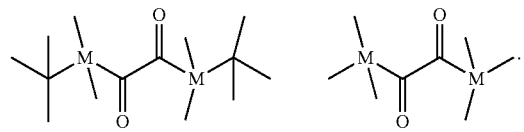

For example, compounds of formula (VIII) wherein $R^\#$ represents a group of formula (X) wherein Y is a bond, an oxygen atom or a $NR^{19}$ group, and $R^{18}$ represents a substituted or unsubstituted hydrocarbyl group may have the following structural formulae:

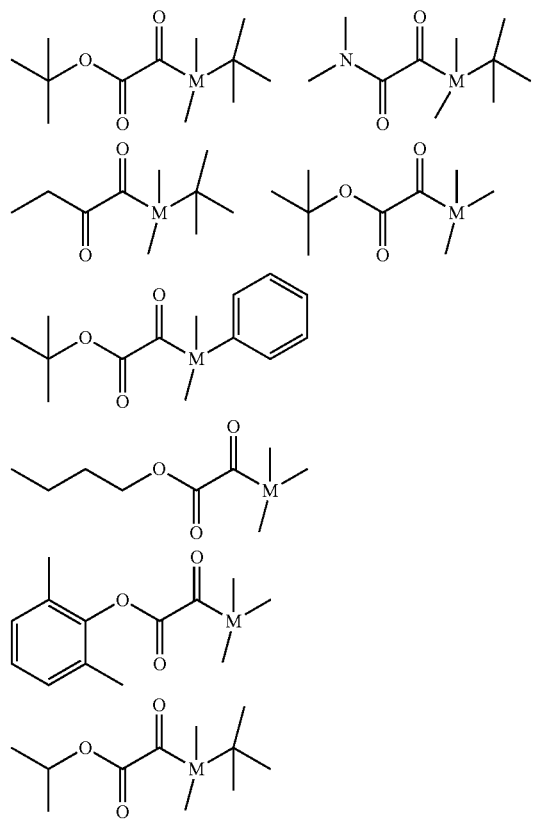

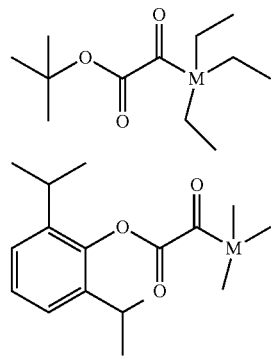

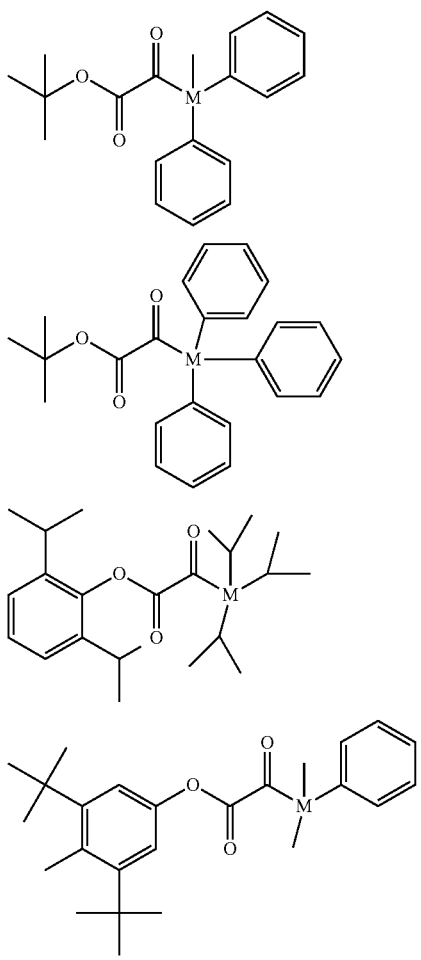
For example, compounds of formula (VIII) wherein $R^{\#}$ represents a group of formula (X) wherein $R^{18}$ represents a trihydrocarbylsilyl group have the following structural formulae:
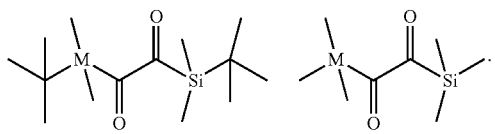
For example, compounds of formula (VIII) wherein M is Si and R represents a substituted or unsubstituted hydrocarbyl group, may have the following structural formulae:
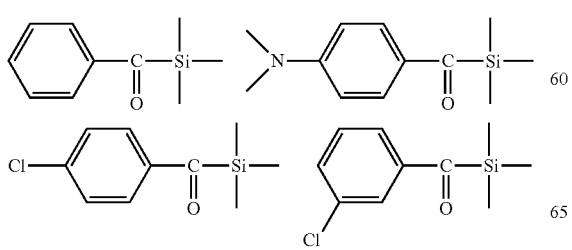
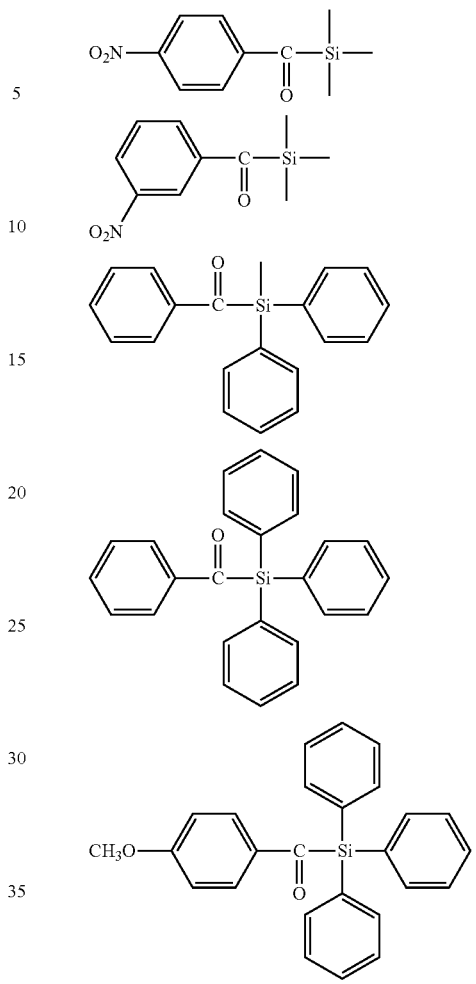
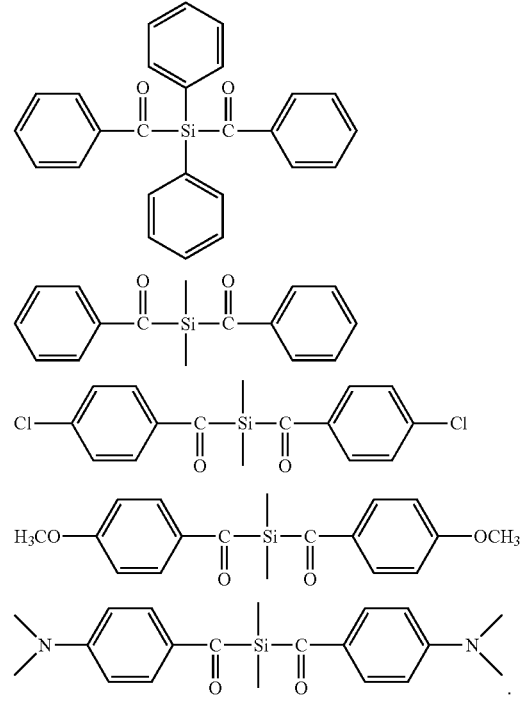

Preferably, compound of formula (VIII) is selected from the group consisting of:

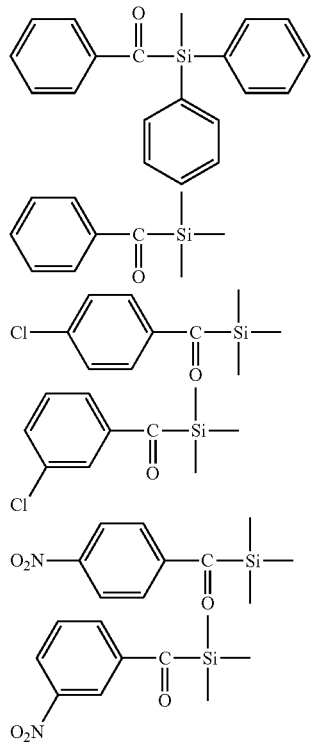

wherein compounds of formula (VIII) with M=Si are particularly preferred.

Most preferably, compound of formula (VIII) is selected from the group consisting of:

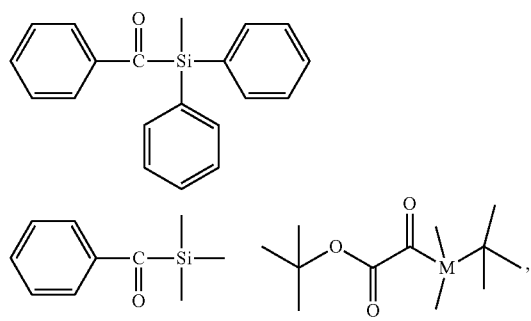

wherein it is particularly preferred that M=Si.

The compound of the formula (VIII) may be a known compound which is commercially available or a may be prepared according to published procedures.

The compound of formula (VIII) wherein M is Si and $R^{\#}$ represents a substituted or unsubstituted hydrocarbyl group may for example be readily prepared by means of a one-step Pd-catalyzed reaction with a disilane as described e.g. by Yamamoto K. at al., *J. Tetrahedron Lett.*, 1980, vol. 21, pages 1653 to 1656:

Scheme 3: Preparation of acylsilanes

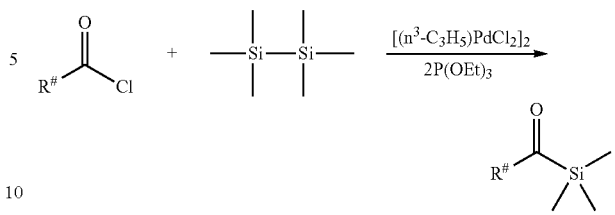

In Scheme 3, the reaction is exemplary depicted with hexamethylsilan as the disilane, whereby a compound of formula (VIII) wherein $R^{15}$, $R^{16}$ and $R^{17}$ represent a methyl group is obtained. It is understood that $R^{15}$, $R^{16}$ and $R^{17}$ can be varied by applying disilanes having hydrocarbon substituents other than methyl.

The compound of formula (VIII) wherein $R^{\#}$ represents a group of formula (X) in which Y is an oxygen atom and $R^{18}$ represents a hydrocarbyl group may for example be prepared by a three-step synthesis as described by Nicewicz D. A. et al. in *Org. Synth.*, 2008, 85, pages 278 to 286. In this three-step synthesis, an acetoacetate is converted to an azide compound, which is then reacted with a trihydrocarbylsilyl-trifluoromethane-sulfonate to obtain a trihydrocarbylsilyldi-azoacetate, which is finally reacted with potassium peroxy-monosulfate to arrive at the target compound:

Scheme 4: Preparation of silylgloyoxylates

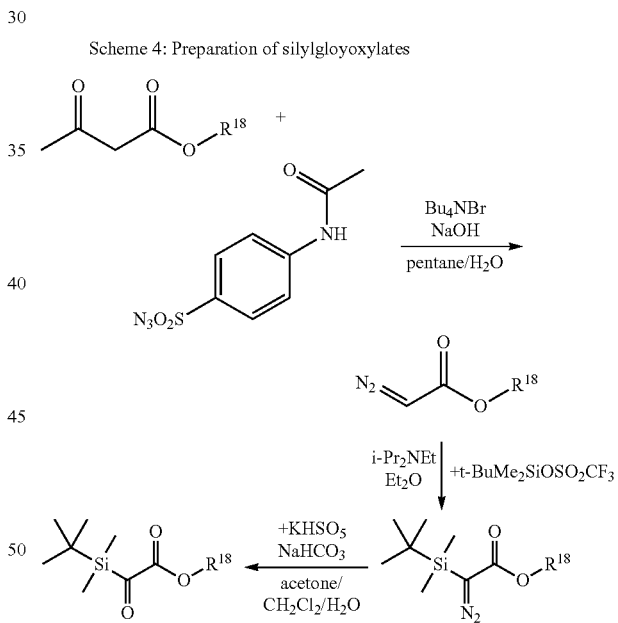

In Scheme 4, the reaction is exemplary depicted for obtaining a compound of formula (VIII) wherein $R^{18}$ of group (X) represents a hydrocarbyl group in the form of tert-butyl. It is understood that $R^{18}$ can be varied by applying an acetoacetate other than tert-butyl acetoacetate.

Alternatively, compounds of formula (VIII) wherein M is Si, R represents a group of formula (X) and Y represents an oxygen atom may be prepared by a single-pot three-component coupling reaction of a silylglyoxylate, a terminal alkyne and an aldehyde in the presence of $ZnI_2$ and $Et_3N$ as described by Nicewicz D. A. in J. Am. Chem. Soc., 2005, 127 (17), pages 6170 to 6171. Further syntheses of silylg-lyoxylate compounds are described e.g. by Boyce G. R. at al.

In *J. Org. Chem.*, 2012, 77 (10), pages 4503 to 4515 and Boyce G. R. et al. in Org. Lett., 2012, 14 (2), pages 652 to 655.

For example, the following compounds of formula (VIII) are known and commercially available, and their Chemical Abstracts (CAS) No. is given in brackets: benzoyltriphenylsilane (1171-49-9), benzoyltrimethylsilan (5908-41-8), 1-[(trimethylsilyl) carbonyl]-naphthalene (88313-80-8), 1-methoxy-2-[(trimethysilyl)-carbonyl]-benzene (107325-71-3), (4-chlorobenzoyl) (triphenyl) silane (1172-90-3), (4-nitrobenzoyl) (triphenyl) silane (1176-24-5), (methyldiphenylsilyl)phenyl-methanone (18666-54-1), (4-methoxybenzoyl) triphenylsilan (1174-56-7) and tert-butyl (tert-butyldimethylsilyl)glyoxylate (852447-17-7).

All compounds of formula (VIII) comprise the group of formula (IX),

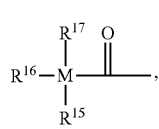

(IX)

wherein M, $R^{15}$, $R^{16}$ and $R^{17}$ are defined as above. Depending on the selection of M, the group of formula (IX) represents an acylsilane or acylgermane group. Upon exposure to UV-VIS-light, the bond between M and the acyl group may be cleaved, whereby a silyl/germanyl and an acyl radical is formed as a polymerization initiating structure, but in competition to the cleavage into to radicals, a carbene structure might be formed:

Scheme 5: carbene formation versus radical formation

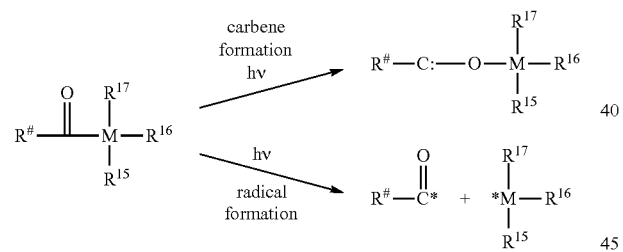

This competition between the formation of polymerization initiating radicals and carbene formation is described for acylsilanes by El-Roz, M. et al. in Current Trends in Polymer Science, 2011, vol. 15, pages 1 to 13.

Besides, in case in compound of formula (VIII) wherein $R^{\#}$ has the same meaning as $X^{\#}$ or is a group of formula (X), the C—C bond of the 1,2-diketone moiety (—C(=O)—C(=O)—) may be cleaved upon exposure to UV-VIS-light into two acyl radicals. This cleavage is exemplary shown for compound of formula (VIII) wherein R is a group of formula (X) and Y is an oxygen atom, that is for a glyoxylate (—O—C—O)—C(=O)—) compound:

Scheme 6: cleavage of —O—C(=O)—C(=O)— moiety of a glyoxylate

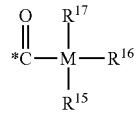

Besides, in compound of formula (VIII), there is a third possibility for a radical cleavage in case $R^{\#}$ is a compound of formula (X) wherein Y is an oxygen atom and $R^{18}$ is a substituted or unsubstituted hydrocarbyl group. Namely, an intra- or intermolecular hydrogen abstraction might occur, where a hydrogen radical is abstracted:

Scheme 7: hydrogen abstraction (intra- or intermolecular)

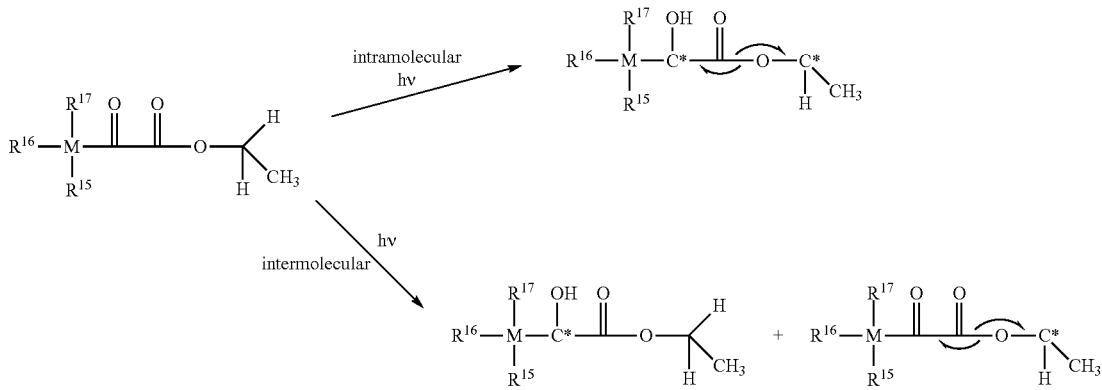

Both the cleavage of a glyoxylate group and the hydrogen abstraction mechanism is known for photosensitizers which do not contain silicium or germanium, such as ethyl phenylglyoxylate (Irgacure® MBF).

For compounds of formula (VIII) wherein $R^\#$ has the same meaning as $X^\#$ or is a group of formula (X), the present inventors carried out molecular modelling calculations from which it appears that a Si—C or Ge—C bond cleavage can be ruled out, since the C—C bond of the —C(=O)—C (=O)— moiety is weaker than the Si—C or Ge—C bond.

The compounds of formula (VIII) represent photosensitizers. Specifically, they may act as Norrish type I photosensitizers and thus may be used alone, or in combination with an optional coinitiator.

Preferably, the photosensitizer is camphor quinone, 2,4-6-trimethylbenzoyl-diphenylphosphine oxide (Irgacure® TPO) or a compound of formula (VIII). Most preferably, the photosensitizer is a compound of formula (VIII).

The photosensitizer is used together with an iodonium salt as a coinitiator. Examples of iodonium salts have the following formula:

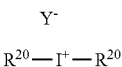

wherein the $R^{20}$ which may be the same or different represent an aryl group which may be substituted, and $Y^-$ is an anion selected from hexafluoroantimonate, trifluoromethylsulfate, hexafluorophosphate, tetrafluoroborate, hexafluoroarsenate, and tetraphenylborate. In the iodonium salt, $R^{20}$ is preferably a phenyl group which may be substituted with 1 to 3 substituents selected from halogen atoms, a cyano group, a hydroxy group, an amino group, $C_{1-6}$ alkyl groups and $C_{1-6}$ alkoxy groups. $C_{1-6}$ alkyl groups as substituents are preferred.

In particular, there is typically a synergistic effect when (b) the photosensitizer is combined with a iodonium salt as defined above. Preferred iodonium salts include diaryl iodonium salts, e.g., diphenyliodonium chloride, diphenyliodonium hexafluorophosphate of the following formula:

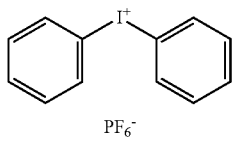

diphenyliodonium tetrafluoroborate, and tolycumyliodonium tetrakis(pentafluorophenyl)borate of the following formula

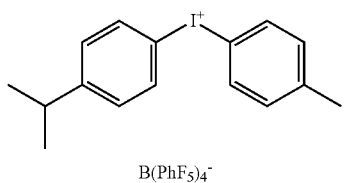 [SMILES: Cc1ccc([I+]c2ccc(C(C)C)cc2)cc1]

and iodonium salts of the following formula:

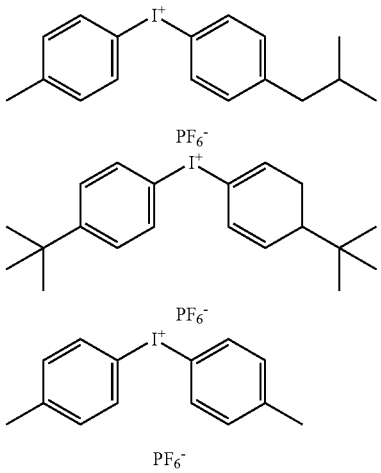

The most preferred iodonium salts are diphenyliodonium hexafluorophosphate, (4-methylphenyl)[4-(2-methylpropyl) phenyl]iodonium hexafluorophosphate (Irgacure® 250, commercial product available from BASF SE).

Further Polymerizable Compounds

Besides of (a) the polymerizable compound of formula (I), the polymerizable dental composition of the present invention may further contain one or more polymerizable compounds having a polymerizable double bond other than compound of formula (I). Preferably, the one or more compounds having a polymerizable double bond each contain one or two radical-polymerizable groups.

Further compounds having a polymerizable double bond are preferably selected from the group of (meth)acrylates.

Suitable (meth)acrylates may be selected from the group of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, 2-propenoic acid 2-methyl 1,1'-[(1-methylethylidene)bis[4,1-phenyleneoxy(2-hydroxy-3,1-propanediyl)]]ester also termed bisphenol A glycerolate dimethacrylat ("bis-GMA", CAS-No. 1565-94-2), 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxyethyl ester (CAS no. 72869-86-4) (UDMA), glycerol mono- and di-acrylate, glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxy-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned.

Besides of the above listed (meth)acrylates, the polymerizable dental composition may also comprise urethane (meth)acrylates, epoxy (meth) acrylates and polyol (meth)acrylates.

Other suitable examples of compounds having a polymerizable double bond are isopropenyl oxazoline, vinyl azalactone, vinyl pyrrolidone, styrene and divinylbenzene.

It is preferable that the amount of the one or more polymerizable compounds of formula (I) and the further one or more compounds having a polymerizable double bond is 5 to 80% by weight relative to the entire polymerizable dental composition, more preferably 10 to 60% by weight.

Coinitiators

The polymerizable dental composition according to the present invention may further comprise one or more coinitiators for improving the photopolymerization efficiency of the photosensitizer (b).

Preferably, the polymerizable dental composition according to the present invention comprises a coinitiator in the form of an amine. The dental composition may comprise one or more amine coinitiator(s).

The amine coinitiator is not particularly limited, as long as it is capable of donating electrons in a photochemical process, for example by means of electron lone pairs.

Preferably, the amine coinitiator is a tertiary amine selected from the group consisting of trialkanolamine, 4-N,N-dialkylaminobenzonitrile, alkyl N,N-dialkylaminobenzoate, alkyl N,N-dialkylaminobenzoate, N,N-dialkylaminoethyl alkylacrylate and isoamyl 4-N,N-dialkylaminobenzoate, N,N-dialkylaniline, N,N-dialkytoluidine, N,N-dialkyloltoluidine, dialkylaminoanisole, 1 or 2-dialkylaminonaphthalene. In particular, the tertiary amine is selected from the group consisting of triethanolamine, alkyl 4-N,N-dialkylaminobenzoate, ethyl 4-N,N-dialkylaminobenzoate, 4-N,N-dialkylaminoethyl methacrylate, isoamyl 4-N,N-dialkylaminobenzoate and 4,4'-N,N-bis(dialkylamino)benzophenone. In these amine compounds, the alkyl group may represent a straight chain, branched or cyclic alkyl group. Furthermore, in the amine compound wherein more than one alkyl group is present, the alkyl groups may be the same or different, preferably the are the same. Preferably, the alkyl group is a $C_{1-6}$ alkyl group, more preferably a $C_{1-4}$ alkyl group. Most preferably, the alkyl group is a methyl or ethyl group.

Particular preferred amine coinitiators are tertiary amines selected from the group consisting of triethanolamine, 4-N,N-dimethylaminobenzonitrile, methyl N,N-dimethylaminobenzoate, ethyl N,N-dimethylaminobenzoate (DMABE), N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene. More preferred amine coinitiators are tertiary amines selected from the group consisting of triethanolamine, methyl 4-N,N-dimethylaminobenzoate, ethyl 4-N,N-dimethylaminobenzoate (DMABE), 4-N,N-dimethylaminoethyl methacrylate, isoamyl 4-N,N-dimethylaminobenzoate and 4,4'-N,N-bis(dimethylamino)benzophenone. Most preferably, the amine coinitiator is ethyl 4-N,N-dimethylaminobenzoate (DMABE).

Furthermore, the polymerizable dental composition according to the invention may alternatively or additionally comprise coinitiators other than the above described amine coinitiators.

For example, the coinitiator may also be selected from the group consisting of amides, ethers, thioethers, ureas, thioureas, ferrocene, sulfinic acids and their salts, salts of ferrocyanide, ascorbic acid and its salts, dithiocarbamic acid and its salts, salts of xanthates, salts of ethylene diamine tetraacetic acid, salts of tetraphenylboronic acid, silanes and germanes.

From the above group of coinitiators other than amines, silanes and germanes are preferred, in particular trihydrocarbylsilanes or trihydrocarbylgermanes in which the three hydrocarbylgroups have the same meaning as defined for $R^{15}$, $R^{16}$ and $R^{17}$ of compound of formula (VIII). From these, triphenylsilicium hydride ($Ph_3SiH$) or triphenylgermanium hydride ($Ph_3GeH$) are preferred, and most preferred is triphenylgermanium hydride ($Ph_3GeH$).

Besides, if (b) the photosensitizer is an acylsilane or acylgermanium compound of formula (VIII), the coinitiator may be a photosensitizer other than compound of formula (VIII), such as the diketone and phosphine oxide photoinitiators described above. Such a coinitiator may for example be added to improve the matching of the emission spectrum of dental LED with the absorption of the photo-initiating system. For example, if compound of formula (VIII) does not or not sufficiently absorb light within the range of 450 to 500 nm, it is preferred to add a photosensitizer having a good absorption within this range. Preferably, the coinitiator being a photosensitizer other than compound of formula (VIII) is a 1,2 or 1,3 diketone, more preferably 1,2 diketone, most preferably camphor quinone.

Further Components

Optionally, the dental compositions of the present invention may comprise further components such as a stabilizer, a solvent and/or a particulate filler.

The dental composition may comprise one or more stabilizer(s).

The term "stabilizer" as used herein means any compound capable of preventing polymerizable compounds contained in the dental composition from spontaneous polymerization during storage. However, the stabilizer does not disturb or prevent Intended polymerisation curing of the dental composition during application.

Two groups of stabilizers are known, namely aerobic and anaerobic stabilizers.

Anaerobic stabilizers are stable radicals such as 2,2,6,6-tetramethyl-1-piperidinyloxy (TEMPO), nitones or alkoxyamine radicals, phenothiazine or galvanoxyl radicals.

Aerobic stabilizer may be selected from the group consisting of hydroquinone, hydroquinone monoalkylether, tert-butyl-hydroquinone, tert-butylhydroxyanisol, propyl gallate and 2,6-di-tert-butyl-p-cresol. From these conventional stabilizers, 2,6-di-tert-butyl-p-cresol is preferred.

Preferably, the stabilizer is an aerobic stabilizer, more preferably a compound of the following formula (XI) and/or (XII):

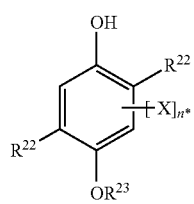

(XI)

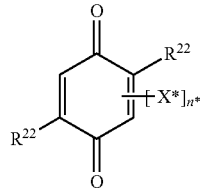

(XII)

wherein the $R^{22}$, which may be the same or different, independently represent a branched $C_{3-8}$ alkyl group or alkenyl or a $C_{3-8}$ cycloalkyl or cycloalkenyl group, $R^{23}$ represents a $C_{1-6}$ alkyl or $C_{2-6}$ alkenyl group, or a $C_{1-6}$ fluoroalkyl or $C_{2-6}$ fluoroalkenyl group, X* represents a group selected from a $C_{1-8}$ alkyl group or a $C_{3-8}$ cycloalkyl group, and n* is 0, 1 or 2.

It was surprisingly found that the class of stabilizers of formula (XI) and/or (XII) provides for full or at least substantial avoidance of discoloration upon storage and/or during photocuring. In particular, this class of stabilizers provides for a surprising stabilizing effect in an acidic aqueous mixture so that a dental composition having a pH of less than 7 may be provided which has no or substantially no discoloration upon storage and an excellent storage stability due to an improved resistance against premature polymerization.

More preferably, the stabilizer is a compound of formula (XI) and/or (XII) wherein the $R^{22}$, which may be the same or different, independently represent a branched $C_{3-8}$ alkyl group or a $C_{3-8}$ cycloalkyl group, and $R^{23}$ represents a $C_{1-6}$ alkyl group or a $C_{1-6}$ fluoroalkyl group, and n* is 0 or 1. Even more preferably, the stabilizer is a compound of formula (XI) and/or (XII) wherein the $R^{22}$, which may be the same or different, independently represent a branched $C_{3-8}$ alkyl group and $R^{23}$ represents a $C_{1-6}$ alkyl group, and n* is 0. Most preferably, the stabilizer is a compound of the following formulae (XIa), (XIb) or (XIIa):

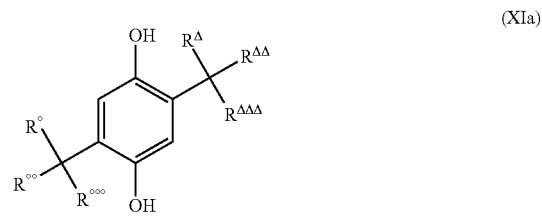

(XIa)

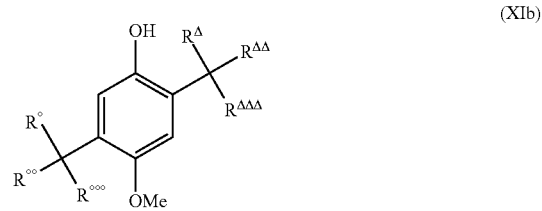

(XIb)

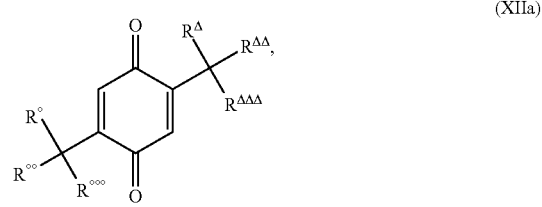

(XIIa)

wherein $R^{\circ}$, $R^{\circ\circ}$, $R^{\circ\circ\circ}$, $R^{\Delta}$, $R^{\Delta\Delta}$ and $R^{\Delta\Delta\Delta}$, which may be the same or different, independently represent an alkyl or an ethyl group. It is particularly preferred that the stabilizer of formulae (XIa), (XIb) or (XIIa) is a compound of the following formulae:

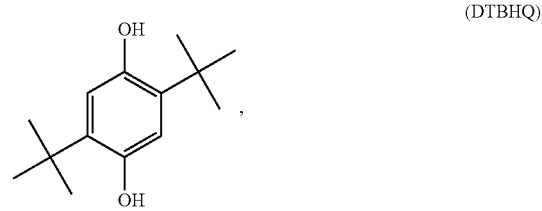

(DTBHQ)

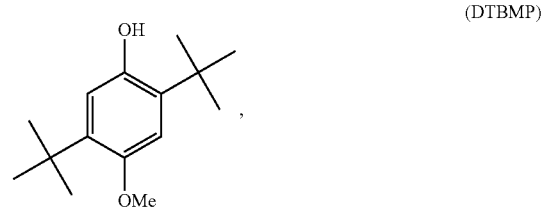

(DTBMP)

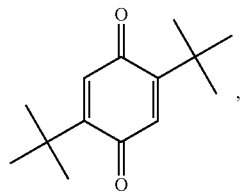

(DTBBQ)

preferably DTBHQ.

The stabilizer DTBHQ is particularly preferred, since from experimental testings it appears that this stabilizer provides the best results in view of the discoloration problematic, i.e. there is no or almost no discoloration of the dental composition upon storage at 50° C. for 30 days.

Discoloration upon storage and/or during photocuring may be determined according to ISO 7491:2000(en).

The dental composition according to the invention contains the stabilizer in an amount of 0.001 to 1 percent by weight, preferably 0.005 to 0.8 percent by weight based on the total weight of the composition. When the amount of the stabilizer is below the above indicated lower limit of 0.001, then storage stability of the dental composition might be Insufficient, since the amount of stabilizer is too small to provide a stabilizing effect. However, when the amount of stabilizer is above the maximum threshold of 1 percent by weight, then the applicability of the dental composition might be negatively affected, since higher amounts of stabilizer may disturb or even substantially prevent intended polymerisation curing of the dental composition during application.

Further, the polymerizable dental composition according to the present invention may comprise suitable solvents. These solvents may be selected from water, alcohols such as methanol, ethanol, propanol (n-, i-), butanol (n-, iso-, tert.-), ketones such as acetone or the like.

The dental composition of the present invention may preferably comprise 5 to 75 percent by weight based on the total weight of the composition of a solvent.

Besides, the polymerizable dental composition according to the present invention may comprise suitable particulate fillers. These particulate fillers may be selected from fillers currently used in dental compositions. The filler should be finely divided and preferably has a maximum particle diameter less than about 10 μm and an average particle diameter less than about 1 μm. The filler may have a unimodal or polymodal (e.g., bimodal) particle size distribution.

The filler can be an Inorganic material. It can also be a crosslinked organic material that Is insoluble in the polymerizable resin, and is optionally filled with Inorganic filler. The filler can be radioopaque. Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles Include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler may also be a filler obtainable by a process for the preparation of composite filler particles, comprising:

(a) coating a particulate filler having a median particle size (D50) of from 1 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently (b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

(c) optionally milling, classifying and/or sieving the granulation of the coated particulate filler; and (d) optionally further crosslinking the granulation of the coated particulate filler; for providing composite filler particles having a median particle size (D50) of from 1 to 70 μm, wherein reactive groups are transformed into crosslinking groups obtained by reacting reactive groups and optionally a further crosslinking agent, and wherein the particulate filler is the main component by volume of the composite filler particles as further described in EP-A 2 604 247.

The dental composition of the present invention may preferably comprise 0.1 to 85 percent by weight based on the total weight of the composition of particulate filler.

The dental compositions of the present invention may further contain preservatives, pigments, free radical scavengers, reactive and nonreactive diluents, coupling agents to enhance reactivity of fillers, rheology modifiers, and surfactants.

Suitable preservatives may be selected from reducing agents such as vitamin C, inorganic sulfides and polysulfides and the like.

Preferred Embodiments

According to a preferred embodiment, the polymerizable dental composition according to the invention comprises:

(a) a polymerizable compound of the following formula (I):

wherein

X' represents a group of the following formula (II) or (III):

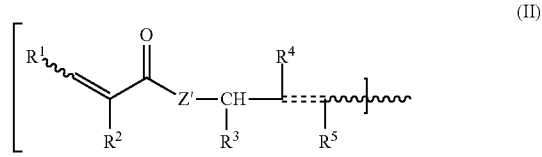

-continued

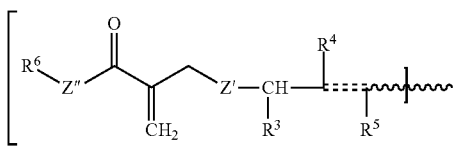

(III)

wherein
the dotted lines represent
a double bond or a triple bond, preferably a double bond,
whereby in case a triple bond is present, $R^4$ and $R^5$ are absent;
the jagged line(s) Indicate(s) that formula (II) and (III) include any (E) or (Z) isomer,
Z' and Z", which may be the same or different, independently represent an oxygen atom or >N—R, wherein
R is a hydrogen atom or a straight-chain $C_{1-4}$ alkyl or $C_{2-4}$ alkenyl group, or a branched or cyclic $C_{3-6}$ alkyl or alkenyl group, which group may be substituted by an acidic group, preferably by a phosphoric acid monoester group (—O—P(=O)(OH)$_2$), or a group of the following formula (IV):

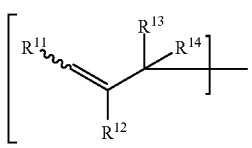

(IV)

wherein
the jagged line Indicates that formula (IV) includes any (E) or (Z) isomer,
preferably R is a group of formula (IV),
$R^{11}$ represents a hydrogen atom or a straight-chain $C_{1-4}$ alkyl or $C_{2-4}$ alkenyl group or a branched or cyclic $C_{3-6}$ alkyl or alkenyl group, preferably a hydrogen atom or a straight-chain $C_{1-4}$ or branched $C_{3-6}$ alkyl group, and
$R^{12}$ represents a hydrogen atom;
$R^{13}$ and $R^{14}$,
which may be the same or different, independently represent a hydrogen atom or a straight-chain $C_{1-4}$ alkyl or $C_{2-4}$ alkenyl group or a branched or cyclic $C_{3-6}$ alkyl or alkenyl group, preferably a hydrogen atom or a straight-chain $C_{1-4}$ or branched $C_{3-6}$ alkyl group, or $R^{13}$ and $R^{14}$ represent together an oxygen atom forming a carbonyl group together with the adjacent carbon atom;
$R^1$ represents a hydrogen atom;
$R^2$ represents a hydrogen atom or a straight-chain $C_{1-4}$ or branched $C_{3-6}$ alkyl group, which group may be substituted by at least one moiety selected from the group consisting of a hydroxyl group, a $C_{1-6}$ alkoxy group and an acidic group, preferably by a $C_{1-6}$ alkoxy group;
$R^3$ represents a hydrogen atom or a straight-chain $C_{1-4}$ alkyl or $C_{2-4}$ alkenyl group or a branched or cyclic $C_{3-6}$ alkyl or alkenyl group, preferably a hydrogen atom or a straight-chain $C_{1-4}$ or branched $C_{3-6}$ alkyl group;
$R^4$ and $R^5$
which may be the same or different, independently represent a hydrogen atom or a straight-chain $C_{1-4}$ or branched $C_{3-6}$ alkyl group, preferably $R^4$ and $R^5$ respectively represent a hydrogen atom;
$R^6$ represents a hydrogen atom or a straight-chain $C_{1-4}$ alkyl or $C_{2-4}$ alkenyl group or a branched or cyclic $C_{3-6}$ alkyl or alkenyl group, preferably a straight-chain $C_{1-4}$ or branched or cyclic $C_{3-6}$ alkyl group, which group may be substituted by a $C_{1-6}$ alkoxy group;
X" represents a moiety of the following formula (V) or (VI):

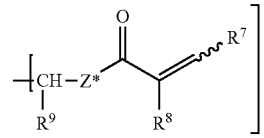

(V)

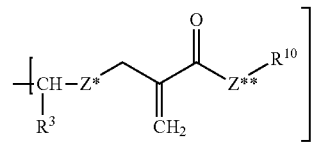

(VI)

wherein
the jagged line indicates that formula (V) includes any (E) or (Z) isomer,
Z* and Z**, which may be the same or different, independently represent an oxygen atom or >N—R', wherein
R' has the same meaning as defined above for R, preferably R' is a group (IV);
$R^7$ is a hydrogen atom;
$R^8$ represents a hydrogen atom or a straight-chain $C_{1-4}$ or branched $C_{3-6}$ alkyl group, which group may be substituted by at least one moiety selected from the group consisting of a hydroxyl group, a thiol group, a $C_{1-6}$ alkoxy group and an acidic group, preferably by a $C_{1-6}$ alkoxy group;
$R^9$ represents a hydrogen atom or a straight-chain $C_{1-4}$ alkyl or $C_{2-4}$ alkenyl group or a branched or cyclic $C_{3-6}$ alkyl or alkenyl group, preferably a hydrogen atom or a straight-chain $C_{1-4}$ or branched $C_{3-6}$ alkyl group;
$R^{10}$ represents a hydrogen atom or a straight-chain $C_{1-4}$ alkyl or $C_{2-4}$ alkenyl group or a branched or cyclic $C_{3-6}$ alkyl or alkenyl group, preferably a hydrogen atom or a straight-chain $C_{1-4}$ or branched $C_{3-6}$ alkyl group;
whereby $R^4$ and R, and/or $R^{11}$ and $R^{13}$ may represent together an alkylene or alkenylene group forming together with the bridging atoms to which they are linked a 3- to 6-membered saturated or unsaturated ring;
whereby $R^9$ and R', and/or $R^{11}$ and $R^{13}$, may represent together an alkylene or alkenylene group forming together with the bridging atoms to which they are linked a 3- to 6-membered saturated or unsaturated ring; and whereby $R^3$ and $R^9$ may represent an alkylene or alkenylene group forming together with the bridging atoms to which they are linked a 4- to 6-membered unsaturated ring; and L which may be present or absent, represents, when present, a divalent linker group of formula (VII)

(VII)

wherein m is 0, n is 0 or 1 and o is 0 or 1, and p is 1, and when L is absent, X' and X" are bonded directly by a single bond; preferably, L is a single bond;

wherein if X' represents a group of formula (II), X" is a group of formula (V), and if X' represents a group of formula (III), X" is a group of formula (VI);

(b) a photosensitizer, and
(c) an iodonium salt.

According to a particularly preferred embodiment, the polymerizable dental composition according to the invention comprises:

(a) a polymerizable compound of the following formula (I):

(I)

wherein

X' represents a group of the following formula (II) or (III):

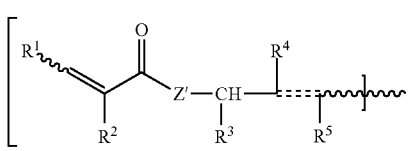
(II)

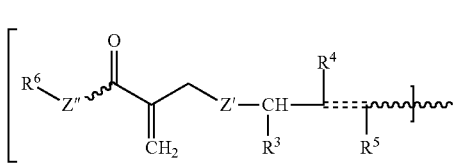
(III)

wherein the dotted lines represents a double bond;

the jagged line(s) indicate(s) that formula (II) and (III) Include any (E) or (Z) isomer, Z' and Z', which may be the same or different, independently represent >N—R, wherein R is a hydrogen atom or a straight-chain $C_{1-4}$ alkyl or $C_{2-4}$ alkenyl group, or a branched or cyclic $C_{3-6}$ alkyl or alkenyl group which group may be substituted by an acidic group, preferably a phosphoric acid monoester group (—O—P(=O)(OH)$_2$), $R^1$ represents a hydrogen atom, $R^2$ represents a hydrogen atom or a straight-chain $C_{1-4}$ or branched $C_{3-6}$ alkyl group, which group may be substituted by a $C_{1-6}$ alkoxy group;

$R^3$ represents a hydrogen atom or a straight-chain $C_{1-4}$ or branched $C_{3-6}$ alkyl group;

$R^4$ and $R^5$, respectively represent a hydrogen atom;

$R^6$ represents a straight-chain $C_{1-4}$ or branched or cyclic $C_{3-6}$ alkyl group, which group may be substituted by a $C_{1-6}$ alkoxy group;

X" represents a moiety of the following formula (V) or (VI):

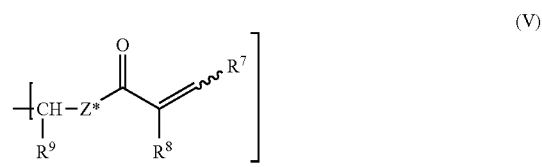
(V)

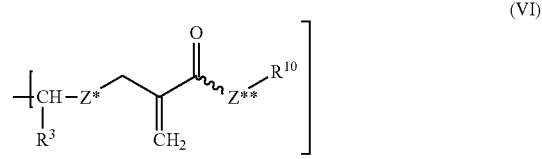
(VI)

wherein the jagged line indicates that formula (V) includes any (E) or (Z) isomer, Z* and Z**, which may be the same or different, independently represent an oxygen atom or >N—R', wherein R' has the same meaning as defined above for R;

$R^7$ is a hydrogen atom, $R^8$ represents a hydrogen atom or a straight-chain $C_{1-4}$ or branched $C_{3-6}$ alkyl group, which group may be substituted by a $C_{1-6}$ alkoxy group;

$R^9$ represents a hydrogen atom or a straight-chain $C_{1-4}$ or branched $C_{3-6}$ alkyl group;

$R^{10}$ represents a hydrogen atom or a straight-chain $C_{1-4}$ alkyl group;

or alternatively, residues R and $R^4$ and/or residues R' and $R^5$, preferably residues R and $R^4$ and residues R' and $R^5$ may represent together an alkylene or alkenylene group forming together with the bridging atoms to which they are linked a 4- to 6-membered saturated or unsaturated ring;

residues $R^3$ and $R^9$ or residues $R^4$ and $R^9$ may represent together a single bond, an alkylene group or an alkenylene group forming together with the bridging atoms to which they are linked a 4- to 6-membered unsaturated ring;

residue $R^{11}$ may represents together with residue $R^{13}$ or $R^{14}$ a single bond or an alkylene or alkenylene group forming together with the bridging atoms to which they are linked 3- to 6-membered unsaturated rings having one or two carbon-carbon-double bonds; and L is a single bond;

wherein if X' represents a group of formula (II), X" is a group of formula (V), and if X' represents a group of formula (III), X" is a group of formula (VI);

(b) a photosensitizer, and
(c) an iodonium salt.

The polymerizable compound of formula (I) as defined in claim 1 may be used for the preparation of a dental composition, preferably of a dental composition according to the invention as described above.

The invention will now be further illustrated by the following Examples.

EXAMPLES

Preparative Examples

Compounds of formula (I) according to the invention having the following structural formulae have been tested:

Scheme 8. Chemical structures of tested compounds of formula (I)

(Ia)
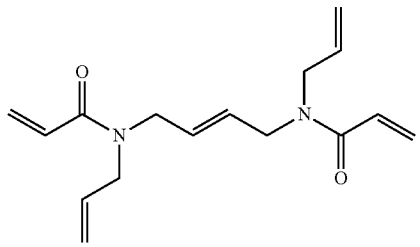

(Ib)
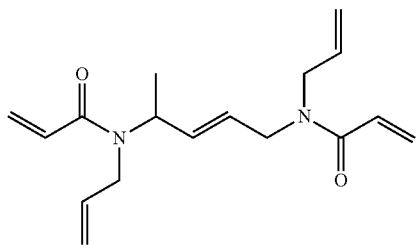

(Ic)
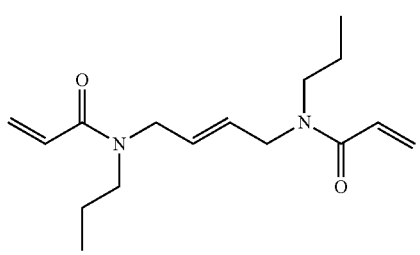

Further, for comparison, compounds having the following structural formulae have been tested which are not according to the present invention:

Scheme 9. Chemical structures of tested polymerizable compounds for comparison (C1)
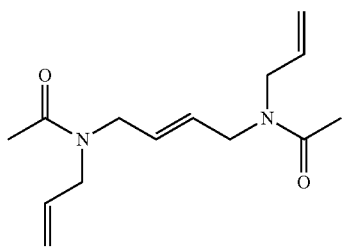

(C2)
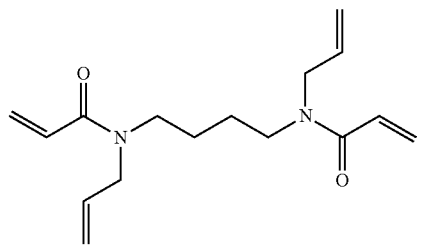

(C3)
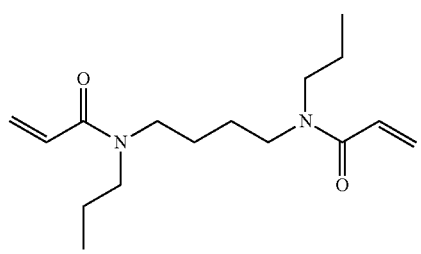

General Procedure for the Synthesis of Compounds of Formula (Ib) and (Ic) and Comparative Compounds (C1), (C2) and (C3)

A) Synthesis of the N,N'-bisalkyl-1,4-butenes

Potassium carbonate (2.5 equiv.) was added to alkyl amine (15 equiv.) and cooled to 0 to 5° C. The corresponding dibromide (1 equiv.) was added in portions, and the resulting mixture was stirred for 3 to 5 hours at room temperature. Then, the remaining amine was removed by distillation, and the resulting residue was suspended in acetone. After filtration of the salts, the acetone was evaporated.

B) Synthesis of the N,N'-bisalkyl-1,4-butanes

The corresponding alkyl chloride (2.1 equiv.) was added dropwise to a solution of 1,4-diaminobutane (1 equiv.) in methanol at 50° C. The resulting mixture was stirred at 60'C for 24 hours. Then, methanol was removed by distillation, and the residue was diluted with 2M NaOH and extracted with DCM. The organic layer was dried ($Na_2SO_4$), and the solvent was evaporated.

Acrylation of N,N'-bisalkyl-1,4-butenes and N,N'-bisalkyl-1,4-butanes

The resulting crude diamine was dissolved in THF, and triethylamine (3.5 equiv.) was added. Acryloylchloride (2.2 equiv) was added dropwise at 0 to 5° C., after which the resulting mixture was stirred for 2.5 hours at room temperature. Then, the THF was evaporated, ethyl acetate was added, and the resulting mixture was washed 3 times with 2N HCl and once with water. The organic layer was dried ($Na_2SO_4$), the solvent was evaporated and the residue was purified by flash chromatography (eluent: ethyl acetate).

N,N'-Bisacryloyl-N,N'-bisallyl-2,4-pent-2-endiamine (Ib)

Yield: 14%; $\eta_{23°\,C.}$=409±0 Pa*s; $n_D$=1.526

$^1$H NMR (CDCl$_3$): δ (ppm)=6.50-6.26 (m, 5H, 2× H$_2$CCHC(O)), 5.84-5.70 (m, 2H, H$_2$CCHCH$_2$), 5.68-5.60 (m, 2H, H$_2$CCHC(O)), 5.61-5.51 (m, 2H, H$_2$CHCCHCH$_2$), 5.31 (m, 1H, HC(CHs)HCCHCH$_2$), 5.25-5.08 (m, 4H, H$_2$CCHCH$_2$), 4.06-3.71 (m, 6H, HC(CH$_3$)HCCHCH$_2$, 2× H$_2$CCHCH$_2$);

$^{13}$C NMR (CDCl$_3$): δ(ppm)=166.4, 166.3, 166.1 (C(O)CHCH$_2$), 135.1-132.8 (H$_2$CCHCH$_2$), 128.5-126.5 (H$_2$CCHC(O), HC(CH$_3$)HCCHCH$_2$), 117.5-116.4 (H$_2$CCHCH$_2$), 50.0 (HC(CH$_3$)HCCHCH$_2$), 49.1-45.5 (H$_2$CCHCH$_2$, H$_2$CHCCHCH$_2$), 18.7, 17.1, 16.8 (HC(CH$_3$)HCCHCH$_2$);

FT-IR: $\tilde{v}_{max}$ [cm$^{-1}$]=3532, 3491, 3080, 2977, 2924, 1644, 1609, 1416, 1362, 1328 1276, 1217, 1184, 1129, 1059, 976, 919, 794.

N,N'-Bisacryloyl-N,N'-bispropyl-1,4-but-2-endiamine (Ic)

Yield: 33%; η$_{23°C.}$=428±3 Pa*s; n$_D^{20}$=1.5095

$^1$H NMR (CDCl$_3$): δ (ppm)=6.54-6.47 (m, 2H, H$_2$CCHC(O)), 6.33-6.25 (m, 2H, H$_2$CCHC(O)), 5.66-5.58 (m, 2H, H$_2$CCHC(O)), 5.56-5.51 (m, 2H, H$_2$CHCCHCH$_2$), 3.99-3.89 (m, 4H H$_2$CHCCHCH$_2$), 3.30-3.18 (m, H$_3$CCH$_2$CH$_2$), 1.54 ('quint', J=7.0, 4 H, H$_3$CCH$_2$CH$_2$), 0.85 (t, J=7.3, 6 H, H$_3$CCH$_2$CH$_2$);

$^{13}$C NMR (CDCl$_3$): δ(ppm)=166.1, 165.9 (C(O)CHCH$_2$), 128.1-127.3 (H$_2$CCHC(O), H$_2$CHCCHCH$_2$), 117.5-116.7 (H$_2$CCHCH$_2$), 49.1-47.4 (H$_3$CCH$_2$CH$_2$, H$_2$CHCCHCH$_2$), 22.5-20.9 (H$_2$CH$_2$CCH$_2$CH$_2$, H$_3$CCH$_2$CH$_2$), 11.2-11.0 (H$_3$CCH$_2$CH$_2$);

FT-IR: $\tilde{v}_{max}$ [cm$^{-1}$]=3525, 2963, 2932, 2875, 1645, 1609, 1442, 1426, 1368, 1279, 1224, 1123, 1059, 975, 888, 794.

COMPARATIVE EXAMPLES

N,N'-Bisacetyl-N,N'-bisallyl-1,4-but-2-endiamine (C1)

Yield: 24%; T$_m$=32° C.; n$_D^{20}$=1.505

$^1$H NMR (CDCl$_3$): δ (ppm)=5.69-5.61 (m, 2H, H$_2$CCHCH$_2$), 5.43 (m, 2H, H$_2$CHCCHCH$_2$), 5.12-4.98 (m, 4H, H$_2$CCHCH$_2$) 3.88-3.74 (m, 8H, H$_2$CHCCHCH$_2$, H$_2$CCHCH$_2$), 2.00 (s, 6H, C(O)CH$_3$)

$^{13}$C NMR (CDCl$_3$): δ(ppm)=170.3-169.4 (C(O)CHs), 132.9-132.3 (H$_2$CCHCH$_2$), 127.9-127.0 (H$_2$CHCCHCH$_2$), 116.7-116.2 (H$_2$CCHCH$_2$), 49.9-46.2 (H$_2$CCHCH$_2$, H$_2$CHCCHCH$_2$) 21.1-21.0 (C(O)CH$_3$);

FT-IR: $\tilde{v}_{max}$ [cm$^{-1}$]=3074, 3012, 2986, 2916, 1633, 1468, 1411, 1360, 1242, 1187, 1035, 978, 919.

N,N'-Bisacryloyl-N,N'-bisallyl-1,4-butandiamine (C2)

Yield: 35%; η$_{23°C.}$=382±1 Pa*s; n$_D^{20}$=1.515

$^1$H NMR (CDCl$_3$): δ (ppm)=6.58-6.28 (m, 4 H$_2$CCHC(O)), 5.80-5.71 (m, 2H, H$_2$CCHCH$_2$), 5.68-5.60 (m, 2H, H$_2$CCHC(O)), 5.21-5.10 (m, 4H, H$_2$CCHCH$_2$), 4.02-3.93 (m, 4H, H$_2$CCHCH$_2$), 3.41-3.40 (m, 4H, H$_2$CH$_2$CCH$_2$CH$_2$), 1.55 (m, 4H, H$_2$CH$_2$CCH$_2$CH$_2$);

$^{13}$C NMR (CDCl$_3$): δ(ppm)=166.6, 166.0 (C(O)CHCH$_2$), 133.3, 133.0 (H$_2$CCHCH$_2$), 128.2-127.5 (H$_2$CCHC(O)), 117.1-116.7 (H$_2$CCHCH$_2$), 50.1-48.6 (H$_2$CCHCH$_2$), 46.9-45.9 (H$_2$CH$_2$CCH$_2$CH$_2$), 26.5-25.0 (H$_2$CH$_2$CCH$_2$CH$_2$);

FT-IR: $\tilde{v}_{max}$=[cm$^{-1}$]=3472, 3082, 2924, 1646, 1609, 1428, 1374, 1217, 1163, 1133, 1059, 978, 957, 918, 794.

N,N'-Bisacryloyl-N,N'-bispropyl-1,4-butandiamine (C3)

Yield: 28%; η$_{23°C.}$=486±1 Pa*s; n$_D^{20}$=1.515

$^1$H NMR (CDCl$_3$): δ (ppm)=6.40-6.33 (m, 2H, H$_2$CCHC(O)), 6.16-6.09 (m, 2H, H$_2$CCHC(O)), 5.49-5.43 (m, 2H, H$_2$CCHC(O)), 3.21-3.05 (m, 8H$_2$CH$_2$CCH$_2$CH$_2$, H$_3$CCH$_2$CH$_2$), 1.38 (m, 8H, H$_3$CCH$_2$CH$_2$, H$_2$CH$_2$CCH$_2$CH$_2$), 0.70 (m, H$_3$CCHCH$_2$);

13C NMR (CDCl$_3$): δ(ppm)=165.5, 165.4 (C(O)CHCH$_2$), 127.5-126.9 (H$_2$CCHC(O)), 49.1-45.3 (H$_3$CCH$_2$CH$_2$, H$_2$CH$_2$CCH$_2$CH$_2$), 26.3-20.5 (H$_2$CH$_2$CCH$_2$CH$_2$, H$_3$CCH$_2$CH$_2$), 10.9-10.6 (H$_3$CCH$_2$CH$_2$);

FT-IR: $\tilde{v}_{max}$ [cm$^{-1}$]=3314, 2963, 2933, 2874, 1645, 1608, 1481, 1449, 1426, 1374, 1263, 1227, 1166, 1136, 1058, 978, 954, 794.

Differential Scanning Calometry (DSC) Experiments

For DSC experiments, compositions containing compound of formula (Ib), (Ic), (C1), (C2) or (C3), 0.22 to 0.35 mol-% of a stabilizer, 0.3 wt.-% camphor quinone (CQ) as photosensitizer and 0.4 wt.-% 4-(dimethylamino) benzoic acid ethylester (DMABE) as coinitiator were provided. In these compositions, the indication mol-% is based on the molar amount of compound of formula (Ib), (Ic), (C1), (C2) or (C3), and the indication wt.-% is based on the total weight of the composition, wherein the remaining mass/weight of the composition is made up of compound of formula (Ib), (Ic), (C1), (C2) or (C3). The compositions were irradiated at 37° C. with SmartLite Focus LED curing light from Dentsply with an Intensity of 100 mW/cm$^2$, and DSC was carried out with the apparatus Perkin Elmer DSC 7/DPA 7.

Figure 2:
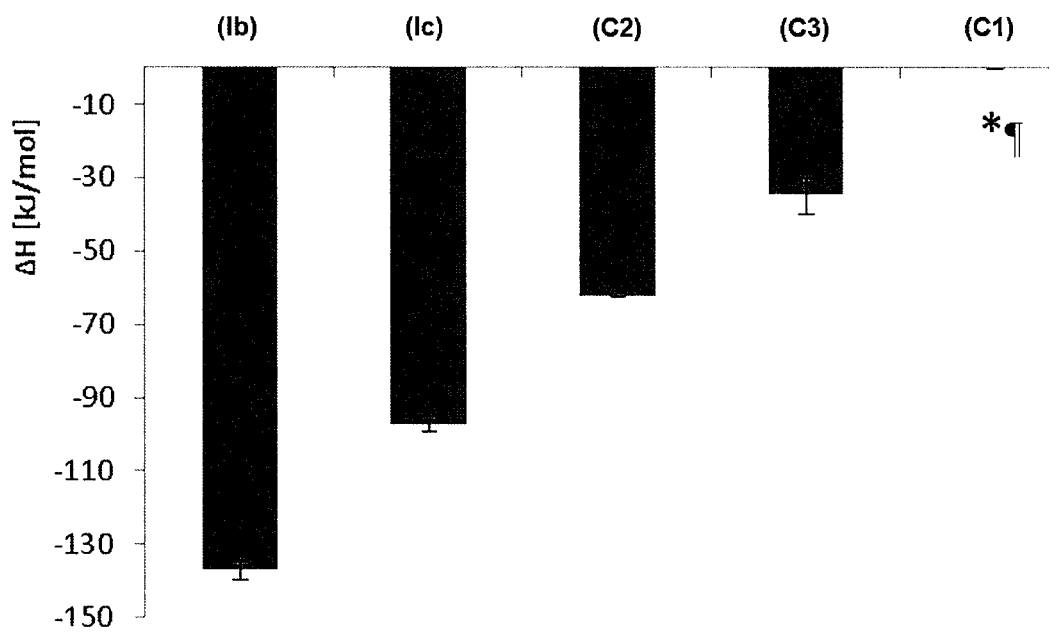
FIG. 2 shows a bar diagram for the polymerization enthalpy (ΔH)

Results:

The DSC measurement results listed in Table 1 and depicted in FIG. 2 show that compounds of formula (Ia), (Ib) and (Ic) according to the present Invention have a favorable polymerization enthalpy which is comparable to the polymerization enthalpy of (meth)acrylates conventionally used in dental compositions, which is typically about Δ$_R$H=−80 to −120 kJ/mol. Furthermore, as can be gathered from Tables 1 and 2 below, compounds of formula (Ia), (Ib) and (Ic) have an advantageous viscosity, color, odour, solubility and refractive index for use in the preparation of polymerizable dental compositions. The parameters refractive Index (RI) and viscosity are depicted in FIG. 1.

TABLE 1

Experimental results for compounds of formula (Ia), (Ib) and (Ic).

| Compound | color | odour | solubility | | n$_D^{20}$ | η$_{23°C.}$ [mPa · s] | Amount stabilizer [mol-%] | ΔHØ*) ± standard deviation |
|---|---|---|---|---|---|---|---|---|
| (Ia) | slightly yellow | acrylate like, low intensity | water<br>EtOH<br>iPrOH<br>acetone<br>methacrylic acid | −)<br>++<br>++<br>++*)<br>++ | 1.5290 | 338.0 ± 0.0 | 0.22-0.28 | −152.905 ± 13.61 |

TABLE 1-continued

Experimental results for compounds of formula (Ia), (Ib) and (Ic).

| Compound | color | odour | solubility | | $n_D^{20}$ | $\eta_{23°C.}$ [mPa · s] | Amount stabilizer [mol-%] | $\Delta H\emptyset^*) \pm$ standard deviation |
|---|---|---|---|---|---|---|---|---|
| (Ib) | almost colorless | fruity, sweet, pleasant, very low intensity | water EtOH iPrOH acetone methacrylic acid | – ++ ++ ++ ++ | 1.5260 | 409.0 ± 0.0 | 0.25-0.35 | –136.79 ± 5.28 |
| (Ic) | almost colorless | slightly sharp, low intensity | water EtOH iPrOH acetone methacrylic acid EtOH iPrOH acetone methacrylic acid | – ++ ++ ++ ++ ++ ++ ++ ++ | 1.5095 | 427.5 ± 2.5 | 0.25-0.35 | –97.345 ± 3.10 |

Figure 3:
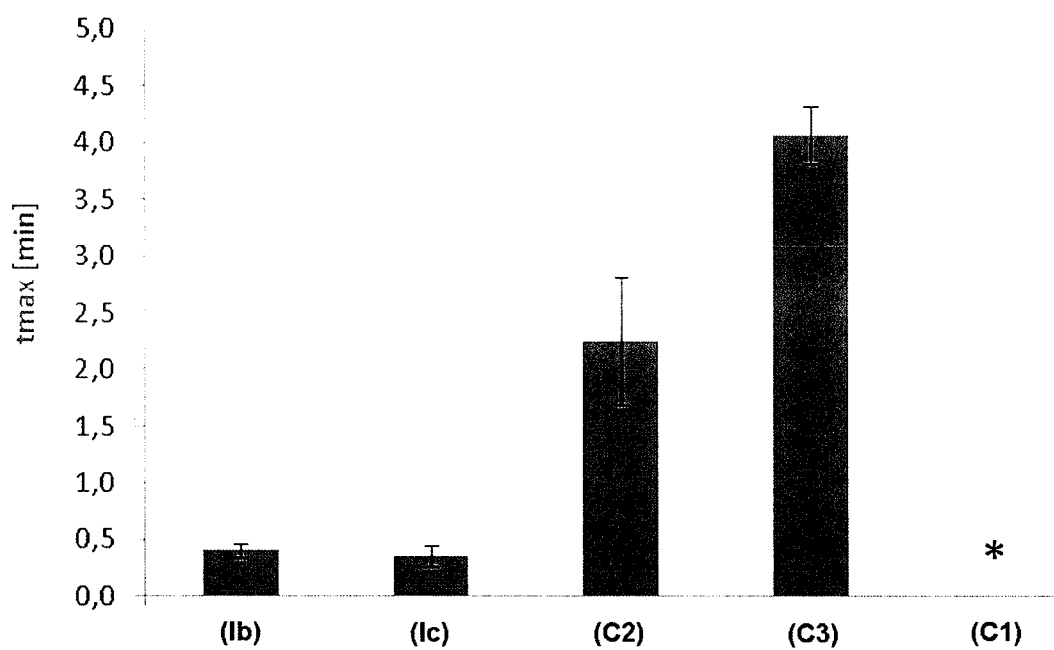
FIG. 3 shows a bar diagram for the time of the maximum heat flow ($t_{max}$), that is the time taken to reach the highest polymerization rate. Both ΔH and $t_{max}$ were determined for a composition respectively containing a compound of formula (Ib), (Ic) or comparative compounds (C1), (C2) or (C3), 0.22 to 0.35 mol-% stabilizer, 0.3 wt.-% camphor quinone (CQ) as photosensitizer, and 0.4 wt.-% 4-(dimethylamino) benzoic acid ethylester (DMABE) as coinitiator. For compound of formula (C1), no ΔH and no $t_{max}$ was detected (indicated by "*")
Figure 4:
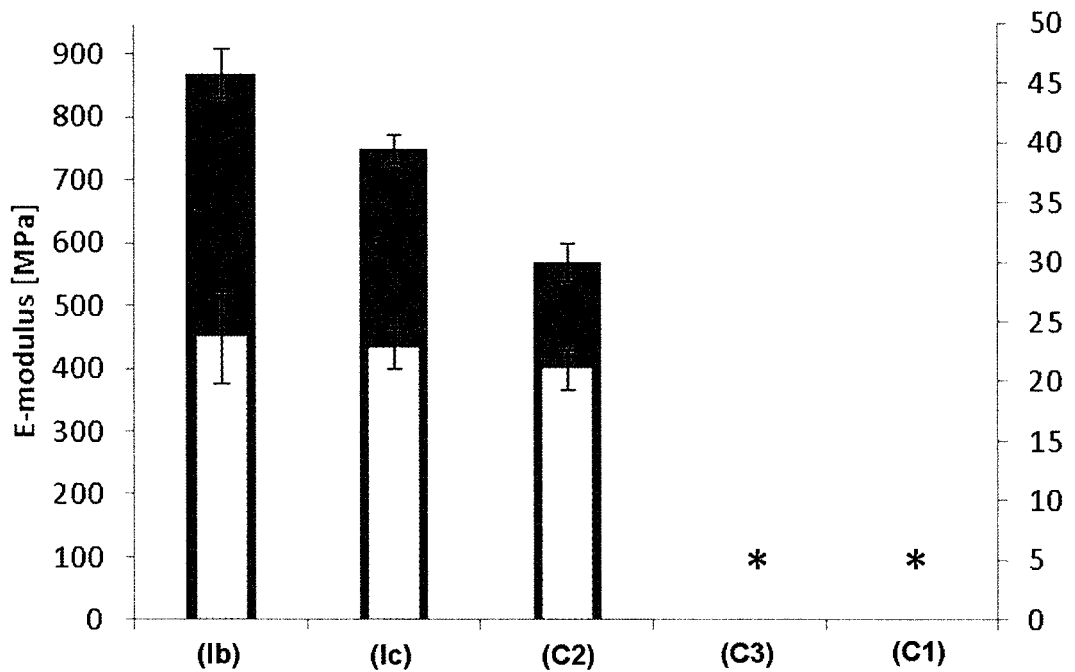
FIG. 4 shows a bar diagram for the E-modulus and flexural strength (FS) determined for the cured composition of Figures and 3.

*)determined at 37° C.
**)"–" means NO solubility
*)"++" means VERY GOOD solubility Besides of the characteristics listed in Table 1, for compounds (Ia), (Ib) and (Ic), the parameters maximum rate of polymerization ($Rp_{max}$), time of the maximum heat flow ($t_{max}$) (see FIG. 3 for compounds (Ib) and (Ic)), flexural strength and e-modulus (see FIG. 4** for compounds (Ib) and (c)) were determined, which are listed in Table 2 below:

| Compound | $Rp_{max\_\emptyset}$/mg | $t_{max\_\emptyset}$ | flexural strength [MPa] | E-modulus [MPa] |
|---|---|---|---|---|
| (Ia) | –100.13 | 0.34 | 17.15 | 1040 |
| (Ib) | –34.14 | 0.409 | 23.69 | 870 |
| (Ic) | –21.75 | 0.35 | 22.83 | 750 |

The DSC measurement results obtained for comparative compounds (C1), (C2) and (C3) are listed in Table 3 below. The results show that comparative compound (C2) may have a favorable polymerization enthalpy which is comparable to the polymerization enthalpy of (meth)acrylates typically used in dental compositions, while the polymerization enthalpy of comparative compound (C3) is outside the desired value range of –80 to –120 kJ/mol for providing compatibility with conventional (meth)acrylates. For comparative compound (C1), polymerization enthalpy was not determined, since this compound failed in pre-tests for determining E-modulus and flexural strength. Furthermore, as can be gathered from Table 4 below, comparative compounds (C2) and (C3) have a maximum rate of polymerization ($Rp_{max}$) which is significantly lower compared to that of compounds of formula (Ia), (Ib) and (Ic) according to the invention. Besides, time of the maximum heat flow ($t_{max}$) of comparative compounds (C2) and (C3) is significantly higher compared to $t_{max}$ of compounds of formula (Ia), (Ib) and (Ic) according to the invention. Further, the E-modulus of a cured dental composition based on comparative compound (C2) is significantly lower compared to that of a cured dental composition based on compounds (Ia), (Ib) and (Ic) according to the invention. Besides, comparative compound (C2) has the drawback that it is not soluble in alcohols like ethanol or isopropanol, but only in the tested solvents acetone and methacrylic acid.

Details of the characteristics obtained for comparative compounds (C1), (C2) and (C3) can be gathered from Tables 3 and 4 below.

TABLE 3

Experimental results for comparative compounds of formula (C1), (C2) and (C3).

| Compound | color | odour | solubility | | $n_D^{20}$ | $\eta_{23°C.}$ [mPa · s] | Amount stabilizer [mol-%] | $\Delta H_\emptyset^*) \pm$ standard deviation |
|---|---|---|---|---|---|---|---|---|
| (C1) | white solid | acrylate like, low intensity | water EtOH iPrOH acetone methacrylic acid | – ++ ++ ++ ++ | solid compound, mp = 32° C. | | 0.25 | n.d.#) |
| (C2) | medium yellow | acrylate like, fruity, pleasant, low intensity | water EtOH iPrOH water/alcohol acetone methacrylic acid | – – – – ++ ++ | 1.5150 | 382.0 ± 1.0 | 0.28-0.35 | –62.35 ± 0.07 |

TABLE 3-continued

Experimental results for comparative compounds of formula (C1), (C2) and (C3).

| Compound | color | odour | solubility | | $n_D^{20}$ | $\eta_{23°C.}$ [mPa·s] | Amount stabilizer [mol-%] | $\Delta H_\Theta^{*)} \pm$ standard deviation |
|---|---|---|---|---|---|---|---|---|
| C3) | orange, intense | sharp fruity, apple- like, too intense | water EtOH iPrOH acetone methacrylic acid | – ++ ++ ++ ++ | 1.5150 | 485.5 ± 0.5 | 0.25-0.35 | −34.70 ± 10.01 |

)"n.d." means "not determined
*)determined at 37° C.
**) "–" means NO solubility
***) "++" means VERY GOOD solubility Besides of the characteristics listed in Table 3, for the liquid comparative compounds of formula (C2) and (C3), the parameters maximum rate of polymerization ($Rp_{max}$), time of the maximum heat flow ($t_{max}$) ($t_{max}$) (see FIG. 3), flexural strength and e-modulus (see FIG. 4) were determined, which are listed in Table 4 below:

| Compound | $Rp_{max\_\varnothing}$/mg | $t_{max\_\varnothing}$ | flexural strength [MPa] | e-modulus [MPa] |
|---|---|---|---|---|
| (C2) | −2.20 | 2.26 | 21 | 570 |
| (C3) | −0.19 | 4.06 | — | — |

Figure 5:
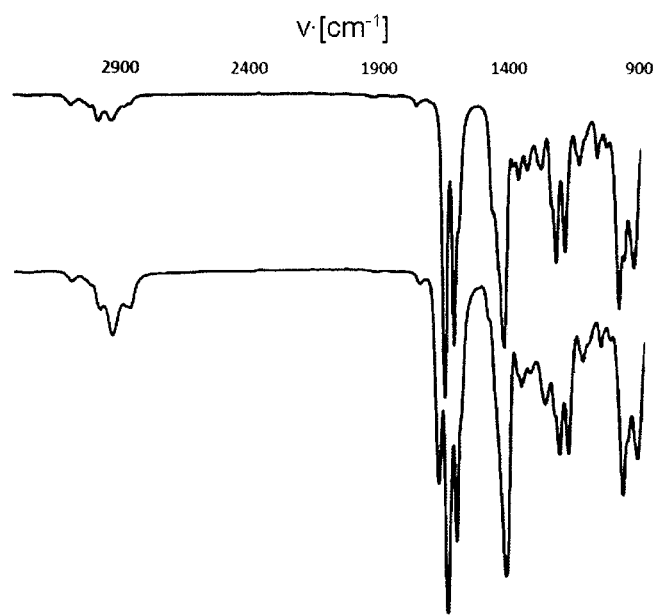
FIGS. 5 to 9 show FT-IR-spectra before and after polymerization of the indicated compounds of formula (Ib) (see FIG. 5) and (Ic) (see FIG. 6) and comparative compounds (C2) (see FIG. 7), (C3) (see FIG. 8) and (C1) (see FIG. 9). In each of FIGS. 5 to 9, the lower spectrum is recorded before polymerization, and the upper spectrum is recorded after polymerization.
Figure 6:
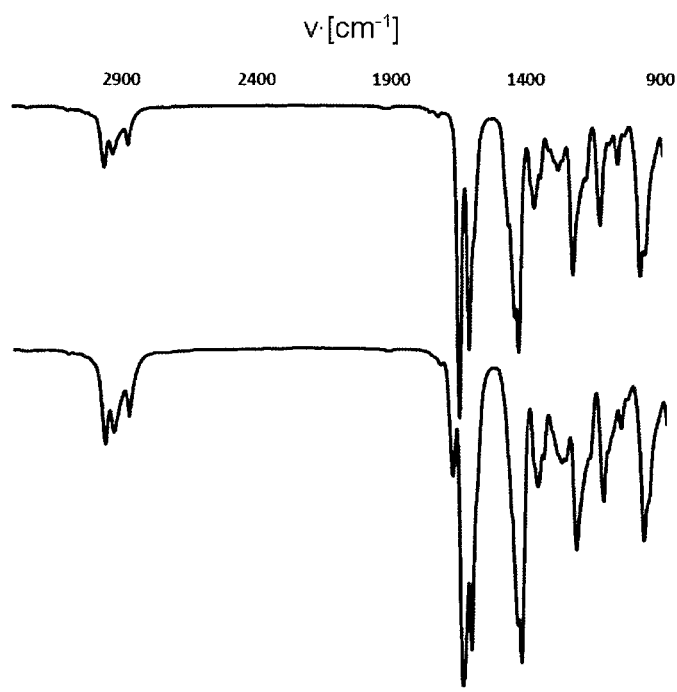
Figure 7:
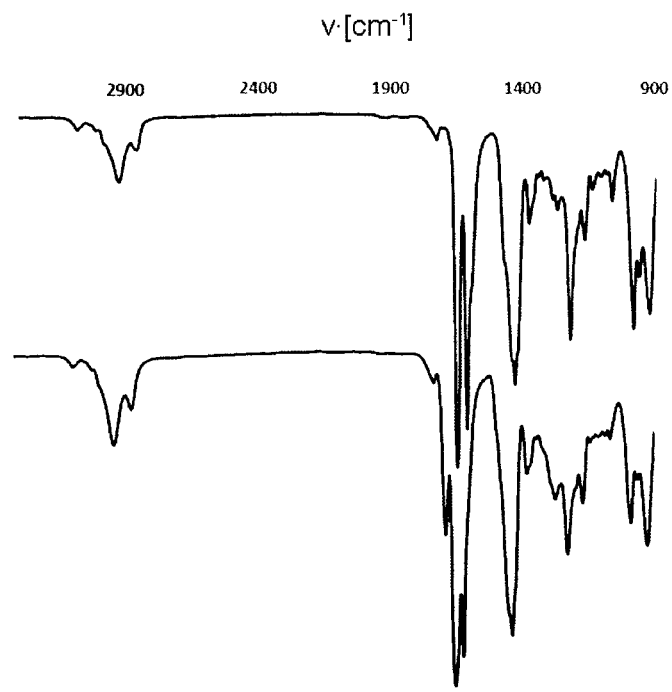
Figure 8:
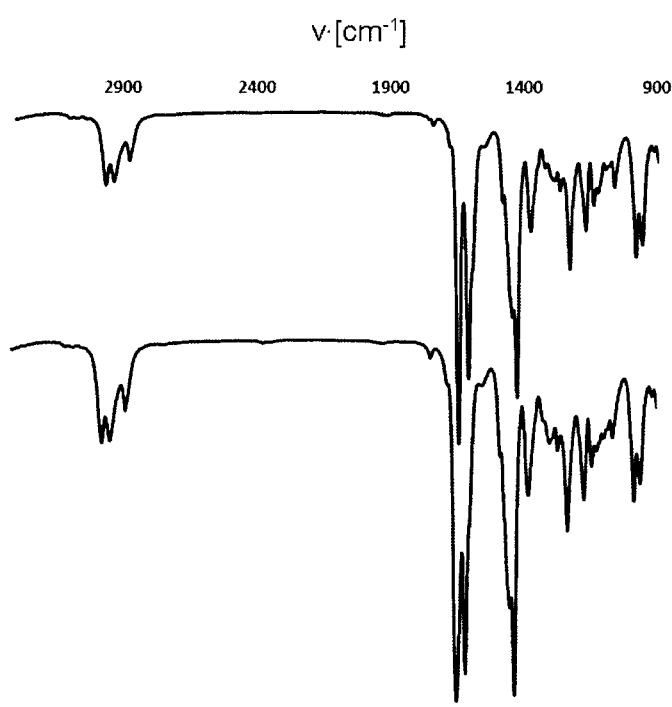
Figure 9:
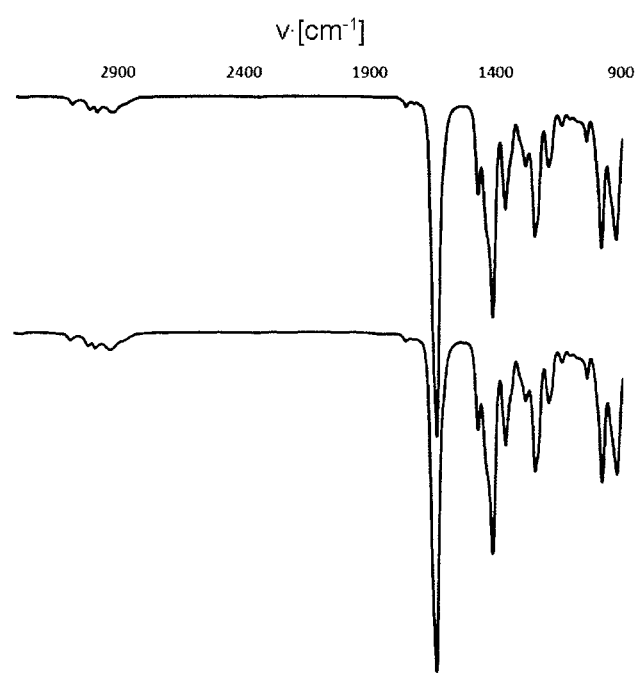

The IR spectra of compound of formula (Ib) depicted in FIG. 5 and of comparative compound (C2) depicted in FIG. 7 show that in the upper spectrum recorded before polymerisation, there are two bands in the range of v=1.500-1800 cm$^{-1}$: at about 1.650 cm$^{-1}$ and at about 1.610 cm$^{-1}$. After polymerization, as can be gathered from the lower spectrum of FIGS. 5 and 7, one band appears in the range of v=1.500-1800 cm$^{-1}$, and three bands remain: at about 1.660 cm$^{-1}$ (C=O), about 1.620 cm$^{-1}$ (allyl C=C), and about 1.600 (acryloyl C=C). The band at about 1.650 cm$^{-1}$ appears to be an amide I band (C=O), and the band about 1.610 is an amide II (N—H). Without wishing to be bound to theory, it is believed that the amide I and II bonds are indicative for the formation of cyclopolymerization, that is formation of a δ-lactam ring as described above in connection with Scheme 1.

In conclusion, the above experimental examples support that the present polymerizable compounds of formula (I) have a polymerization enthalpy which renders possible their polymerization together with conventional (meth)acrylates, (meth)acrylamides and allylic ethers typically used in dental compositions. Further, compounds of formula (I) have an advantageous viscosity, color, odour, solubility and refractive Index making them particularly suitable for use in the preparation of polymerizable dental compositions.

Example 1

M-BAABE (bis-N,N'-Methacryloyl-, Lot.: MS1261), yield: 29%

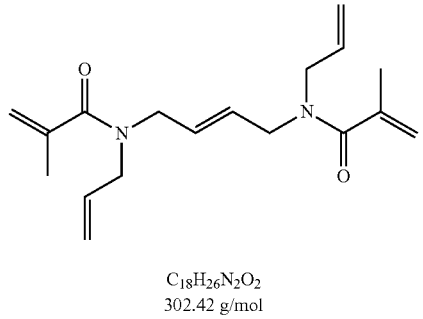 [SMILES: C=CCN(C/C=C/CN(CC=C)C(=O)C(=C)C)C(=O)C(=C)C]

$C_{18}H_{26}N_2O_2$
302.42 g/mol $^1$H NMR (CDCl$_3$): δ (ppm)=5.79-5.68 (m, 2H, H$_2$CC HCH$_2$), 5.59-5.46 (m, 2H, H$_2$CHCCHCH$_2$), 5.23-5.09 (m, 4H, H$_2$CCHCH$_2$), 5.14 (s, 2H, H$_2$CC(CH$_3$)C(O)) 5.04 (s, 2H, H$_2$CC(CH$_3$)C(O)), 4.00-3.89 (m, 8H$_2$CHCCHCH$_2$, H$_2$CCHCH$_2$); 1.95 (s, 6H, 2×Me)

$^{13}$C NMR (CDCl$_3$): δ(ppm)=162.5 (C(O)C(CH$_3$)CH$_2$), 140.6 (2×H$_2$CCHCH$_2$), 133.5-132.6 (H$_2$CC(CH$_3$)C(O)), 128.7-128.1 (H$_2$CHCCHCH$_2$), 117.7-116.2 (H$_2$CCHCH$_2$), 50.5-48.6 (H$_2$CCHCH$_2$), 46.7-45.2 (H$_2$CHCCHCH$_2$), 20.6 (Me)

Me2DPI

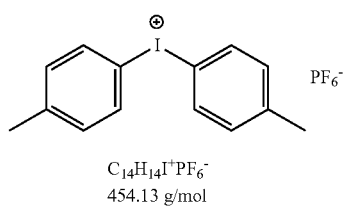

$C_{14}H_{14}I^+PF_6^-$
454.13 g/mol

Formulations

The adhesive formulations 1 and 2 were prepared by mixing the individual components as shown in Table 5.

TABLE 5

Composition of the adhesive formulations

| | | Application Example 1 | Application Example 2 |
|---|---|---|---|
| | | Formulation # | |
| Adhesive | | 1 | 2 |
| M-BAABE | wt-% | 36.6 | 44.6 |
| MDP | wt-% | 12.2 | 11.0 |
| 2-Propanol | wt-% | 16.0 | 15.0 |
| Water | wt-% | 20.2 | 19.1 |
| Camphor quinone | wt-% | 1.6 | 1.6 |
| Dimethylamino benzonitrile | wt-% | 0.7 | 0.7 |
| Me2DPI | wt-% | 0.8 | 0.8 |
| Other resin components, stabilizer | wt-% | 11.9 | 7.2 |
| Sum | wt-% | 100.0 | 100.0 |

| Abr. | Substance name | CAS No. |
|---|---|---|
| M-BAABE | N,N'-(2E)-but-2-en-1,4-diallylbis-[(N-isobut-2-en-1) amide] | — |
| MDP | 2-methyl-, 10-(phosphonooxy)decyl ester 2-propenoic acid | 85590-00-7 |
| Me2DPI | bis(4-methylphenyl)iodonium hexafluoro-phosphate | 60565-88-0 |

Preparation

The liquids were mixed in the ratio given in Table 1 and stirred for 2 hours at 22° C. in closed vessels and under yellow-light conditions.

Application

All solutions were applied on pre-conditioned, roughened surfaces (enamel and dentin) of human molar teeth in both, Self-Etch (without pre-etching) and Etch&Rinse mode (with phosphoric acid for pre-etching) using the following steps: spreading using a applicator microbrush, gently agitating for 20 sec, thoroughly evaporating the solvent for at least 5 sec and finally, blue light curing for 10 sec (minimum output level of 800 mW/cm2). A Spectrum TPH3 (A2) composite post was positioned onto the respective surfaces and blue light cured according to its Instructions for use. The specimens were stored in water at 37'C for 24 h and subsequently, shear-bond-strengths (Table 4) were determined using a Zwick testing machine. The arithmetic average and the standard deviation were calculated from six samples of every composition and on each template (enamel/dentin), respectively.

| Adhesive Shear-Bond-Strength on Template | | Application Example 1 | Application Example 2 |
|---|---|---|---|
| Enamel, Self-Etch mode | MPa | 11.3 ± 1.5 | 10.3 ± 0.9 |
| Dentin, Self-Etch mode | MPa | 16.9 ± 1.4 | |
| Enamel, Etch&Rinse mode | MPa | 22.1 ± 2.0 | 15.0 ± 1.4 |
| Dentin, Etch&Rinse mode | MPa | 23.3 ± 2.8 | 19.3 ± 4.4 |
| pH value | | — | 2.4 | 2.5 |

Ternary Camphor quinone/amine/iodonium salt (BAABE, Me2DPI; Application Example 1) Initiator system vs. binary Camphor quinone/amine initiator system (Comparative Example 1)

Formulations

The adhesive formulations 1 and 2 were prepared by mixing the individual components as shown in Table 6.

TABLE 6

Composition of the adhesive formulations

| | | Application Example 3 | Comparative Example 1 |
|---|---|---|---|
| | | Formulation # | |
| Adhesive | | 3 | 4 |
| BAABE | wt-% | 40.6 | 40.9 |
| MDP | wt-% | 11.6 | 11.7 |
| 2-Propanol | wt-% | 15.5 | 15.7 |
| Water | wt-% | 19.6 | 19.6 |
| Camphor quinone | wt-% | 1.6 | 1.6 |
| Dimethylamino benzonitrile | wt-% | 0.7 | 0.7 |
| Me2DPI | wt-% | 0.8 | 0.0 |
| Other resin components, stabilizer | wt-% | 9.6 | 9.8 |
| Sum | wt-% | 100.00 | 100.00 |

| Abr. | Substance name | CAS No. |
|---|---|---|
| BAABE | N,N'-(2E)-but-2-en-1,4-diallylbis-[(N-prop-2-en-1) amide] | 1620399-32-7 |
| MDP | 2-methyl-, 10-(phosphonooxy)decyl ester 2-propenoic acid | 85590-00-7 |
| Me2DPI | bis(4-methylphenyl)iodonium hexafluoro-phosphate | 60565-88-0 |

| Adhesive Shear-Bond-Strength on Template | | Application Example 3 | Comparative Example 1 |
|---|---|---|---|
| | | 3 | 4 |
| Enamel, Self-Etch mode | MPa | 21.5 ± 3.4 | 15.5 ± 2.2 |
| Dentin, Self-Etch mode | MPa | 30.9 ± 5.2 | 34.4 ± 1.0 |
| pH value | | — | 2.5 | 2.5 |

The invention claimed is:

1. Polymerizable dental composition comprising
(a) a polymerizable compound of the following formula (I):

$$X'\text{-}L\text{-}X'' \qquad (I)$$

wherein
X' represents a group of the following formula (II) or (III):

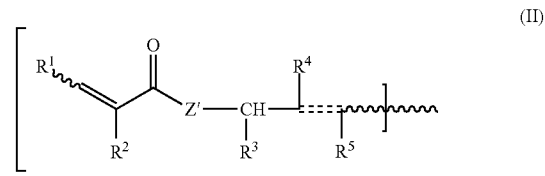

(II)

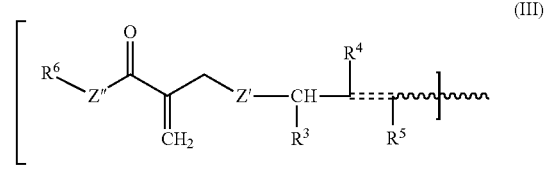

(III)

wherein
the dotted lines represent
a double bond or a triple bond, whereby in case a triple bond is present, $R^4$ and $R^5$ are absent;
the jagged line(s) indicate(s) that formula (II) and (III) include any (E) or (Z) isomer,
Z' and Z", which may be the same or different, independently represent an oxygen atom, a sulfur atom or >N—R, wherein R is a hydrogen atom, a straight-chain, branched or cyclic alkyl or alkenyl group which group may be substituted by an alkoxy or acidic group, or a group of the following formula (IV):

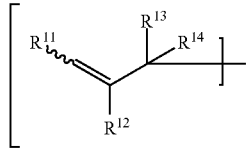

(IV)

wherein
the jagged line indicates that formula (IV) includes any (E) or (Z) isomer,
$R^{11}$ and $R^{12}$,
which may be the same or different, independently represent a hydrogen atom or a straight-chain, branched or cyclic alkyl or alkenyl group, which group may be substituted by an alkoxy group or acidic group;
$R^{13}$ and $R^{14}$,
which may be the same or different, independently represent a hydrogen atom or a straight-chain, branched or cyclic alkyl or alkenyl group, which group may be substituted by an alkoxy or acidic group, or $R^{13}$ and $R^{14}$ represent together an oxygen atom forming a carbonyl group together with the adjacent carbon atom;
$R^1$ and $R^2$,
which may be the same or different, independently represent a hydrogen atom or a straight-chain, branched or cyclic alkyl or alkenyl group, which group may be substituted by at least one moiety selected from the group consisting of a hydroxyl group, an alkoxy group and an acidic group;
$R^3$ represents a hydrogen atom or a straight-chain, branched or cyclic alkyl or alkenyl group, which group may be substituted by an alkoxy or acidic group;
$R^4$ and $R^5$,
which may be the same or different, independently represent a hydrogen atom, a straight-chain, branched or cyclic alkyl or alkenyl group, which group may be substituted by an alkoxy or acidic group;
$R^6$ represents a hydrogen atom or a straight-chain, branched or cyclic alkyl or alkenyl group, which group may be substituted by an alkoxy group;
X" represents a moiety selected from the group consisting of a hydroxyl group, a thiol group, an alkoxy group and an acidic group, or a moiety of the following formula (V) or (VI):

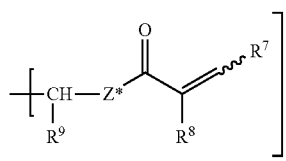

(V)

-continued

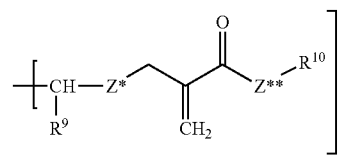

(VI)

wherein
the jagged line indicates that formula (V) includes any (E) or (Z) isomer,
Z* and Z** which may be the same or different, independently represent an oxygen atom, a sulfur atom or >N—R', wherein
R' is a hydrogen atom, a straight-chain, branched or cyclic alkyl or alkenyl group which group may be substituted by an alkoxy or acidic group, or R' independently is a group of the formula (IV) as defined for R;
$R^7$ and $R^8$,
which may be the same or different, independently represent a hydrogen atom, a straight-chain, branched or cyclic alkyl or alkenyl group, which group may be substituted by at least one moiety selected from the group consisting of a hydroxyl group, a thiol group, an alkoxy group and an acidic group;
$R^9$ represents a hydrogen atom or a straight-chain, branched or cyclic alkyl or alkenyl group, which group may be substituted by an alkoxy or acidic group;
$R^{10}$ represents a hydrogen atom or a straight-chain, branched or cyclic alkyl or alkenyl group, which group may be substituted by an alkoxy group;
or alternatively,
any two residues of $R^1$, $R^2$, $R^3$, $R^4$, $R^5$, $R^6$, R, $R^7$, $R^8$, $R^9$, $R^{10}$, R', and if present, $R^{11}$, $R^{12}$, $R^{13}$ and $R^{14}$ may represent together an alkylene or alkenylene group, which may be substituted by an alkoxy group, an acidic group or a —NR▲R▼ group wherein R▲ and R▼ independently from each other represent a hydrogen atom or an alkyl group; or
any two residues of $R^1$, $R^2$, $R^3$, $R^4$, $R^5$, $R^6$, R, $R^7$, $R^8$, $R^9$, $R^{10}$, R', and if present, $R^{11}$, $R^{12}$, $R^{13}$ and $R^{14}$, which are not geminal or vicinal groups, may represent together a single bond,
wherein said single bond or said optionally substituted alkylene or alkenylene group form together with the bridging atoms to which the residues are linked a 3- to 8-membered saturated or unsaturated ring,
wherein the polymerizable compound of formula (I) may comprise one or more of said 3- to 8-membered saturated or unsaturated ring(s); and
L which may be present or absent, represents, when present, a divalent linker group, and when absent X' and X" are bonded directly by a single bond;
(b) a photosensitizer, and
(c) an iodonium salt;
wherein the dental composition does not contain N,N'-diallyl-1,4-bisacrylamido-(2E)-but-2-en (BAABE);
wherein the dental composition when cured, has a flexural strength of at least 22 MPa.

2. The dental composition according to claim 1, wherein $R^{13}$ and $R^{14}$ in R and/or R' represent together an oxygen atom forming a carbonyl group together with the adjacent carbon atom.

3. The dental composition according to claim 1, further comprising (d) a coinitiator.

4. The dental composition according to claim 1, wherein L is a group of the following formula (VII)

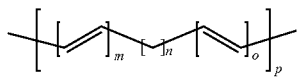

(VII)

wherein
m, n and o, which may be the same or different are integers of from 0 to 3; and p is 0, 1 or 2.

5. The dental composition according to claim 4, wherein p is 0.

6. The dental composition according to claim 4, wherein p is 1.

7. The dental composition according to claim 4, wherein n is 0.

8. The dental composition according to claim 6, wherein m or o is 0.

9. The dental composition according to claim 1, further comprising a stabilizer, a solvent and/or a particulate filler.

10. The dental composition according to claim 1, wherein the dental composition is selected from a groups consisting of a dental adhesive, a dental primer, a dental resin modified glass ionomer cement, a pit and fissure sealer, a dental composite, and a dental flowable.

11. The dental composition according to claim 1, wherein the polymerizable compound of the following formula (I) has a refractive index in a range of from 1.500 to 1.580.

12. The dental composition according to claim 1, wherein the acidic group is selected from a group consisting of a carboxylic acid group, a sulfonic acid group, a phosphonic acid group, and a phosphoric acid monoester group (—O—P(=O)(OH)$_2$).

* * * * *